(12) United States Patent
Long et al.

(10) Patent No.: US 9,464,056 B2
(45) Date of Patent: *Oct. 11, 2016

(54) FUNGICIDAL 4-METHYLANILINO PYRAZOLES

(71) Applicant: E. I. DU PONT DE NEMOURS AND COMPANY, Wilmington, DE (US)

(72) Inventors: Jeffrey Keith Long, Wilmington, DE (US); James Francis Bereznak, Newtown Square, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/410,321

(22) PCT Filed: Jun. 18, 2013

(86) PCT No.: PCT/US2013/046220
§ 371 (c)(1),
(2) Date: Dec. 22, 2014

(87) PCT Pub. No.: WO2013/192126
PCT Pub. Date: Dec. 27, 2013

(65) Prior Publication Data
US 2015/0307456 A1 Oct. 29, 2015

Related U.S. Application Data

(60) Provisional application No. 61/663,268, filed on Jun. 22, 2012.

(51) Int. Cl.
*C07D 231/38* (2006.01)
*A01N 43/56* (2006.01)

(52) U.S. Cl.
CPC ............. *C07D 231/38* (2013.01); *A01N 43/56* (2013.01)

(58) Field of Classification Search
None
See application file for complete search history.

(56) References Cited

U.S. PATENT DOCUMENTS 9,107,412 B2 * 8/2015 Long .................. A01N 43/48

OTHER PUBLICATIONS

Patani et al, Chemical Reviews, 1996, vol. 96, No. 8, p. 3152.*

* cited by examiner

*Primary Examiner* — Kamal Saeed
(74) *Attorney, Agent, or Firm* — Charlene Gross Sternberg

(57) ABSTRACT

Disclosed are compounds of Formula 1, including all stereoisomers, N-oxides, and salts thereof,

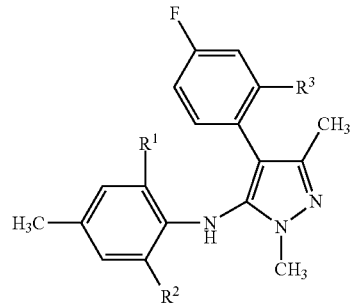

wherein
$R^1$ is F, Cl or Br;
$R^2$ is H, F, Cl or Br; and
$R^3$ is F, Cl or Br.

This invention also relates to a fungicidal composition comprising (a) a compound of Formula 1 including all stereoisomers, N-oxides, and salts thereof (i.e. in a fungicidally effective amount); and (b) at least one additional fungicidal compound (e.g., at least one other fungicide having a different site of action). Also disclosed are process intermediate compounds of Formulae 22, 18 and 20 which are useful for preparing a compound of Formula 1.

8 Claims, No Drawings

FUNGICIDAL 4-METHYLANILINO PYRAZOLES

FIELD OF THE INVENTION

This invention relates to certain 4-methylanilino pyrazole fungicidal compounds, their N-oxides, salts, their compositions, and the intermediates useful in preparing them.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action. Patent application publication WO 2010/101973 A1 discloses certain fungicidal pyrazoles and WO 2012/031061 discloses certain compositions. The compounds and compositions of the present invention are not disclosed in these publications.

SUMMARY OF THE INVENTION

This invention is directed to a compound of Formula 1 (including all stereoisomers), N-oxides, and salts thereof, agricultural compositions containing them and their use as fungicides:

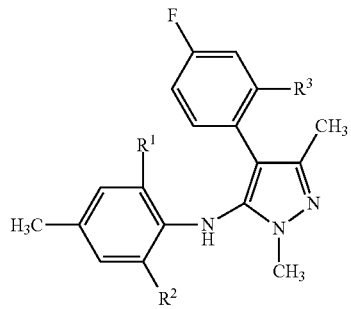

wherein
  $R^1$ is F, Cl or Br;
  $R^2$ is H, F, Cl or Br; and
  $R^3$ is F, Cl or Br.

This invention also relates to a fungicidal composition comprising (a) a compound of Formula 1 including all stereoisomers, N-oxides, and salts thereof (i.e. in a fungicidally effective amount); and (b) at least one additional fungicidal compound (e.g., at least one other fungicide having a different site of action).

This invention also relates to a fungicidal composition comprising: (a) at least one compound selected from a compound of Formula 1 (i.e. in a fungicidally effective amount), (b) at least one fungicidal compound and further comprising (c) at least one additional compound or agent that is biologically active.

This invention also relates to a composition comprising one of the aforesaid compositions comprising components (a) and (b) and at least one additional component selected from the group consisting of surfactants, solid diluents and liquid diluents.

This invention also relates to a method for controlling plant diseases caused by fungal plant pathogens comprising applying to the plant or portion thereof, or to the plant seed, a fungicidally effective amount of one of the aforesaid compositions.

This invention further relates to a compound of Formula 22

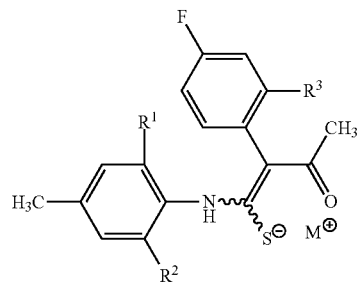

wherein
  $R^1$ is F, Cl or Br;
  $R^2$ is H, F, Cl or Br; and
  $R^3$ is F, Cl or Br; and
  M is Na or K.

This invention further relates to a compound of Formula 18

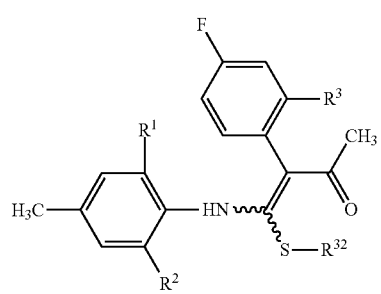

wherein
  $R^1$ is F, Cl or Br;
  $R^2$ is H, F, Cl or Br;
  $R^3$ is F, Cl or Br; and
  $R^{32}$ is H, $CH_3$, $CH_2CH_3$ or $(CH_2)_2CH_3$.

This invention further relates to a compound of Formula 20

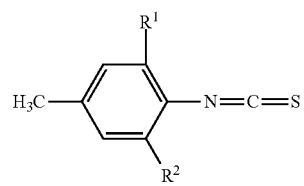

wherein
  $R^1$ is F, Cl or Br; and
  $R^2$ is H, F, Cl or Br.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of"

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds. As referred to herein, the term "seedling", used either alone or in a combination of words means a young plant developing from the embryo of a seed.

As referred to in this disclosure, the terms "fungal pathogen" and "fungal plant pathogen" include pathogens in the Basidiomycete, Ascomycete, Oomycete and Deuteromycete classes that are the causal agents of a broad spectrum of plant diseases of economic importance, affecting ornamental, turf, vegetable, field, cereal and fruit crops. In the context of this disclosure, "protecting a plant from disease" or "control of a plant disease" includes preventative action (interruption of the fungal cycle of infection, colonization, symptom development and spore production) and/or curative action (inhibition of colonization of plant host tissues).

As used herein, the term "alkylating agent" refers to a chemical compound in which a carbon-containing radical is bound through a carbon atom to leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for the 4-methyl group on the aniline moiety (i.e. as shown in Scheme 1).

In the recitations herein, the term "alkyl", used either alone or in compound words such as "alkylthio" or "haloalkyl" includes straight-chain or branched alkyl such as methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" also includes moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkoxyalkyl" denotes alkyl substitution on an alkoxy moiety. Examples include $CH_3CH_2CH_2OCH_2$— and $CH_3CH_2OCH_2CH_2$—. "Alkoxyalkenyl" and "alkoxyalkynyl" designate alkenyl and alkynyl substitution, respectively, on an alkoxy moiety. Examples of "alkoxyalkenyl" include $CH_2=CH_2CH_2OCH_2$ and $CH_2=CH_2CH_2OCH_2CH_2$. Examples of "alkoxyalkynyl" include $CH\equiv CHCH_2OCH_2$ and $CH\equiv CHCH_2OCH_2CH_2$.

In Formula b46.10, an epoxide ring can be formed from the $OR^{b21}$ and $R^{b22}$ groups when taken together with the carbon to which they are attached. This is indicated as "$R^{b21}$ and $R^{b22}$ are taken together as $CH_2$". Examples of "cycloalkylalkyl" include cyclopropylmethyl, cyclopentylethyl, and other cycloalkyl moieties bonded to straight-chain or branched alkyl groups. In Formula b46.10 the term "cycloalkylalkylthio" denotes cycloalkylalkyl linked through a sulfur atom attached to the alkyl chain. Examples of "cycloalkylalkylthio" include cyclopropylmethylthio, cyclopentylethylthio, and other cycloalkyl moieties bonded to straight-chain or branched alkylthio groups. "Alkenylthio" denotes a straight or branched chain alkene moiety bonded through sulfur. Examples of alkenylthio include $CH_2=CH_2CH_2S$— and $CH_2=CH_2CH_2S$—. "Alkynylthio" denotes a straight or branched chain alkyne moiety bonded through sulfur. Examples of alkynylthio include CH≡CHCH₂S— and CH≡CHCH₂CH₂S—.

The term "halogen", either alone or in compound words such as "haloalkyl", or when used in descriptions such as "alkyl substituted with halogen" includes fluorine (i.e F), chlorine (i.e. Cl) or bromine (i.e. Br). Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

One skilled in the art will appreciate that not all nitrogen containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include (where Formula 1 as used in the following Embodiments includes N-oxides and salts thereof): Embodiments of the invention include the following:

Embodiment A1

A compound of Formula 1 described in the Summary of the Invention.

Embodiment A2

A compound of Embodiment A1 wherein $R^1$ is F or Cl.

Embodiment A3

A compound of Embodiment A2 wherein $R^1$ is Cl.

Embodiment A4

A compound of Embodiment A2 wherein $R^1$ is F.

Embodiment A5

A compound of Embodiment A1 wherein $R^2$ is F, Cl or Br.

Embodiment A6

A compound of Embodiment A5 wherein $R^2$ is Cl or Br.

Embodiment A7

A compound of Embodiment A5 wherein $R^2$ is F.

Embodiment A8

A compound of Embodiment A5 wherein $R^2$ is Cl.

Embodiment A9

A compound of Embodiment A5 wherein $R^2$ is Br.

Embodiment A10

A compound of Embodiment A1 wherein $R^3$ is Cl or Br.

Embodiment A11

A compound of Embodiment A10 wherein $R^3$ is Cl.

Embodiment A12

A compound of Embodiment A10 wherein $R^3$ is Br.

Embodiment A13

A compound of Embodiment A1 wherein $R^3$ is F.

Embodiment B1

The composition as described in the Summary of the Invention comprising (a) a compound of Formula 1 (including all stereoisomers), N-oxides, and salts thereof; and (b) at least one additional fungicidal compound.

Embodiment B2

The composition described in Embodiment B1 wherein component (a) comprises a compound of Formula 1 as described in any one of Embodiments A1 through A13.

Embodiment B3

The composition described in Embodiment B2 wherein component (b) comprises at least one fungicidal compound selected from the group consisting of
(b1) methyl benzimidazole carbamate (MBC) fungicides;
(b2) dicarboximide fungicides;
(b3) demethylation inhibitor (DMI) fungicides;
(b4) phenylamide fungicides;
(b5) amine/morpholine fungicides;
(b6) phospholipid biosynthesis inhibitor fungicides;
(b7) carboxamide fungicides;
(b8) hydroxy(2-amino-)pyrimidine fungicides;
(b9) anilinopyrimidine fungicides;
(b10) N-phenyl carbamate fungicides;
(b11) quinone outside inhibitor (QoI) fungicides;
(b12) phenylpyrrole fungicides;
(b13) quinoline fungicides;
(b14) lipid peroxidation inhibitor fungicides;
(b15) melanin biosynthesis inhibitors-reductase (MBI-R) fungicides;
(b16) melanin biosynthesis inhibitors-dehydratase (MBI-D) fungicides;
(b17) hydroxyanilide fungicides;
(b18) squalene-epoxidase inhibitor fungicides;
(b19) polyoxin fungicides;
(b20) phenylurea fungicides;
(b21) quinone inside inhibitor (QiI) fungicides;
(b22) benzamide fungicides;
(b23) enopyranuronic acid antibiotic fungicides;
(b24) hexopyranosyl antibiotic fungicides;
(b25) glucopyranosyl antibiotic: protein synthesis fungicides;
(b26) glucopyranosyl antibiotic: trehalase and inositol biosynthesis fungicides;
(b27) cyanoacetamideoxime fungicides;
(b28) carbamate fungicides;
(b29) oxidative phosphorylation uncoupling fungicides;
(b30) organo tin fungicides;
(b31) carboxylic acid fungicides;
(b32) heteroaromatic fungicides;
(b33) phosphonate fungicides;
(b34) phthalamic acid fungicides;
(b35) benzotriazine fungicides;
(b36) benzene-sulfonamide fungicides;
(b37) pyridazinone fungicides;
(b38) thiophene-carboxamide fungicides;
(b39) pyrimidinamide fungicides;
(b40) carboxylic acid amide (CAA) fungicides;
(b41) tetracycline antibiotic fungicides;
(b42) thiocarbamate fungicides;
(b43) benzamide fungicides;
(b44) host plant defense induction fungicides;
(b45) multi-site contact activity fungicides;
(b46) fungicides other than fungicides of component (a) and components (b1) through (b45); and salts of compounds of (b1) through (b46).

Embodiment B4

The composition described in Embodiment B3 wherein component (b) includes at least one compound selected from (b1) methyl benzimidazole carbamate fungicides such as benomyl, carbendazim and thiophanate-methyl.

Embodiment B5

The composition described in Embodiment B3 wherein component (b) includes at least one compound selected from (b2) dicarboximide fungicides such as procymidone, iprodione and vinclozolin.

Embodiment B6

The composition described in Embodiment B3 wherein component (b) includes at least one compound selected from (b3) demethylation inhibitor fungicides such as epoxiconazole, fluquinconazole, triadimenol, simeconazole, ipconazole, triforine, cyproconazole, difenconazole, flusilazole, flutriafol, metconazole, myclobutanil, prochloraz, propiconazole, prothioconazole, tebuconazole and tetraconazole.

Embodiment B7

The composition described in Embodiment B3 wherein component (b) includes at least one compound selected from (b4) phenylamide fungicides such as metalaxyl, metalaxyl-M, benalaxyl, benalaxyl-M, furalaxyl, ofurace and oxadixyl.

Embodiment B8

The composition described in Embodiment B3 wherein component (b) includes at least one compound selected from (b5) amine/morpholine fungicides such as aldimorph, dodemorph, fenpropimorph, tridemorph, trimorphamide, fenpropidin, piperalin and spiroxamine.

Embodiment B9

The composition described in Embodiment B3 wherein component (b) includes at least one compound selected from (b6) phospholipid biosynthesis inhibitor fungicides such as edifenphos and isoprothiolane.

Embodiment B10

The composition described in Embodiment B3 wherein component (b) includes at least one compound selected from (b7) carboxamide fungicides such as bixafen, boscalid, carboxin, isopyrazam, oxycarboxin, penflufen and penthiopyrad.

Embodiment B11

The composition described in Embodiment B3 wherein component (b) includes at least one compound selected from (b8) hydroxy(2-amino-)pyrimidine fungicides such as ethirimol.

Embodiment B12

The composition described in Embodiment B3 wherein component (b) includes at least one compound selected from (b9) anilinopyrimidine fungicides such as cyprodinil.

Embodiment B13

The composition described in Embodiment B3 wherein component (b) includes at least one compound selected from (b10) N-phenyl carbamate fungicides such as diethofencarb.

Embodiment B14

The composition described in Embodiment B3 wherein component (b) includes at least one compound selected from (b11) quinone outside inhibitor fungicides such as azoxystrobin, pyraclostrobin, pyrametostrobin, kresoxim-methyl, trifloxystrobin, picoxystrobin, pyraoxystrobin, pyribencarb, famoxadone, fenamidone, discostrobin, enestrobin, dimoxystrobin, metominostrobin, orysastrobin and fluoxastrobin.

Embodiment B15

The composition described in Embodiment B3 wherein component (b) includes at least one compound selected from (b12) phenylpyrrole fungicides compound such as fenpiclonil and fludioxonil.

Embodiment B16

The composition described in Embodiment B3 wherein component (b) includes at least one compound selected from (b13) quinoline fungicides such as quinoxyfen.

Embodiment B17

The composition described in Embodiment B3 wherein component (b) includes at least one compound selected from (b14) lipid peroxidation inhibitor fungicides such as chloroneb.

Embodiment B18

The composition described in Embodiment B3 wherein component (b) includes at least one compound selected from (b15) melanin biosynthesis inhibitors-reductase fungicides such as pyroquilon and tricyclazole.

Embodiment B19

The composition described in Embodiment B3 wherein component (b) includes at least one compound selected from (b16) melanin biosynthesis inhibitors-dehydratase fungicides such as carpropamid.

Embodiment B20

The composition described in Embodiment B3 wherein component (b) includes at least one compound selected from (b17) hydroxyanilide fungicides such as fenhexamid.

Embodiment B21

The composition described in Embodiment B3 wherein component (b) includes at least one compound selected from (b18) squalene-epoxidase inhibitor fungicides such as pyributicarb.

Embodiment B22

The composition described in Embodiment B3 wherein component (b) includes at least one compound selected from (b19) polyoxin fungicides such as polyoxin.

Embodiment B23

The composition described in Embodiment B3 wherein component (b) includes at least one compound selected from (b20) phenylurea fungicides such as pencycuron.

Embodiment B24

The composition described in Embodiment B3 wherein component (b) includes at least one compound selected from (b21) quinone inside inhibitor fungicides such as cyazofamid and amisulbrom.

Embodiment B25

The composition described in Embodiment B3 wherein component (b) includes at least one compound selected from (b22) benzamide fungicides such as zoxamide.

Embodiment B26

The composition described in Embodiment B3 wherein component (b) includes at least one compound selected from (b23) enopyranuronic acid antibiotic fungicides such as blasticidin-S.

Embodiment B27

The composition described in Embodiment B3 wherein component (b) includes at least one compound selected from (b24) hexopyranosyl antibiotic fungicides such as kasugamycin.

Embodiment B28

The composition described in Embodiment B3 wherein component (b) includes at least one compound selected from (b25) glucopyranosyl antibiotic: protein synthesis fungicides such as streptomycin.

Embodiment B29

The composition described in Embodiment B3 wherein component (b) includes at least one compound selected from (b26) glucopyranosyl antibiotic: trehalase and inositol biosynthesis fungicides such as validamycin.

Embodiment B30

The composition described in Embodiment B3 wherein component (b) includes at least one compound selected from (b27) cyanoacetamideoxime fungicides such as cymoxanil.

Embodiment B31

The composition described in Embodiment B3 wherein component (b) includes at least one compound selected from (b28) carbamate fungicides such as propamacarb, prothiocarb and iodocarb.

Embodiment B32

The composition described in Embodiment B3 wherein component (b) includes at least one compound selected from (b29) oxidative phosphorylation uncoupling fungicides such as fluazinam, binapacryl, ferimzone, meptyldinocap and dinocap.

Embodiment B33

The composition described in Embodiment B3 wherein component (b) includes at least one compound selected from (b30) organo tin fungicides such as fentin acetate.

Embodiment B34

The composition described in Embodiment B3 wherein component (b) includes at least one compound selected from (b31) carboxylic acid fungicides such as oxolinic acid.

Embodiment B35

The composition described in Embodiment B3 wherein component (b) includes at least one compound selected from (b32) heteroaromatic fungicides such as hymexazole.

Embodiment B36

The composition described in Embodiment B3 wherein component (b) includes at least one compound selected from (b33) phosphonate fungicides such as phosphorous acid and its various salts, including fosetyl-aluminum.

Embodiment B37

The composition described in Embodiment B3 wherein component (b) includes at least one compound selected from (b34) phthalamic acid fungicides such as teclofthalam.

Embodiment B38

The composition described in Embodiment B3 wherein component (b) includes at least one compound selected from (b35) benzotriazine fungicides such as triazoxide.

Embodiment B39

The composition described in Embodiment B3 wherein component (b) includes at least one compound selected from (b36) benzene-sulfonamide fungicides such as flusulfamide.

Embodiment B40

The composition described in Embodiment B3 wherein component (b) includes at least one compound selected from (b37) pyridazinone fungicides such as diclomezine.

Embodiment B41

The composition described in Embodiment B3 wherein component (b) includes at least one compound selected from (b38) thiophene-carboxamide fungicides such as silthiofam.

Embodiment B42

The composition described in Embodiment B3 wherein component (b) includes at least one compound selected from (b39) pyrimidinamide fungicides such as diflumetorim.

Embodiment B43

The composition described in Embodiment B3 wherein component (b) includes at least one compound selected from (b40) carboxylic acid amide fungicides such as dimethomorph, benthiavalicarb, benthiavalicarb-isopropyl, iprovalicarb, valifenalate, mandipropamid and flumorph.

Embodiment B44

The composition described in Embodiment B3 wherein component (b) includes at least one compound selected from (b41) tetracycline antibiotic fungicides such as oxytetracycline.

Embodiment B45

The composition described in Embodiment B3 wherein component (b) includes at least one compound selected from (b42) thiocarbamate fungicides such as methasulfocarb.

Embodiment B46

The composition described in Embodiment B3 wherein component (b) includes at least one compound selected from (b43) benzamide fungicides such as fluopicolide and fluopyram.

Embodiment B47

The composition described in Embodiment B3 wherein component (b) includes at least one compound selected from (b44) host plant defense induction fungicides such as acibenzolar-S-ethyl.

Embodiment B48

The composition described in Embodiment B3 wherein component (b) includes at least one compound selected from (b45) multi-site contact fungicides such as copper oxychloride, copper sulfate, copper hydroxide, Bordeaux mixture (tribasic copper sulfate), elemental sulfur, mancozeb, metiram, propineb, ferbam, maneb, thiram, zineb, ziram, folpet, captan, captafol and chlorothalonil.

Embodiment B49

The composition described in Embodiment B3 wherein component (b) includes at least one compound selected from (b46) fungicides other than fungicides of component (a) and components (b1) through (b45), such as ethaboxam, cyflufenamid, N-[[(cyclopropylmethoxy)amino][6-(difluoromethoxy)-2,3-difluorophenyl]-methylene]benzeneacetamide, proquinazid, metrafenone, ametoctradin, bethoxazin, fluxapyroxad, neo-asozin (ferric methanearsonate), pyriofenone, pyrrolnitrin, quinomethionate, tebufloquin, N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethyl-sulfonyl)amino]butanamide, flutianil (2-[[2-fluoro-5-(trifluoromethyl)-phenyl]thio]-2-[3-(2-methoxyphenyl)-2-thiazolidinylidene]acetonitrile), 3-[5-(4-chlorophenyl)-2,3-dimethyl-3-isoxazolidinyl]pyridine (3-[(3R)-5-(4-chlorophenyl)-2,3-dimethyl-3-isoxazolidinyl]pyridine, pyrisoxazole), 4-fluoro-phenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl)[1,2,4]triazolo[1,5-a]-pyrimidine (BAS600), N-(4-chloro-2-nitrophenyl)-N-ethyl-4-methyl-benzenesulfonamide, N'-[4-[4-chloro-3-(trifluoromethyl)phenoxy]-2,5-dimethylphenyl]-N-ethyl-N-methylmethanimidamide, fenpyrazamine (1-[(2-propenylthio)carbonyl]-2-(1-methylethyl)-4-(2-methylphenyl)-5-amino-1H-pyrazol-3-one), N-[4-[[3-[(4-chlorophenyl)methyl]-1,2,4-thiadiazol-5-yl]oxy]-2,5-dimethylphenyl]-N-ethyl-N-methyl-methanimidamide, 1,1-dimethylethyl N-[6-[[[[(1-methyl-1H-tetrazol-5-yl)phenylmethylene]amino]oxy]methyl]-2-pyridinyl]carbamate, 3-butyn-1-yl N-[6-[[[[(1-methyl-1H-tetrazol-5-yl)-phenylmethylene]amino]oxy]methyl]-2-pyridinyl]carbamate, 2,6-dimethyl-1H,5H-[1,4]dithiino[2,3-c:5,6-c']dipyrrole-1,3,5,7(2H,6H)-tetrone, 5-fluoro-2-[(4-methylphenyl)methoxy]-4-pyrimidinamine and 5-fluoro-2-[(4-fluorophenyl)methoxy]-4-pyrimidinamine.

Embodiment B50

The composition described in Embodiment B3 wherein component (b) includes at least one compound selected from (b46) fungicides other than fungicides of component (a) and components (b1)) through (b45), such as (b46.1),

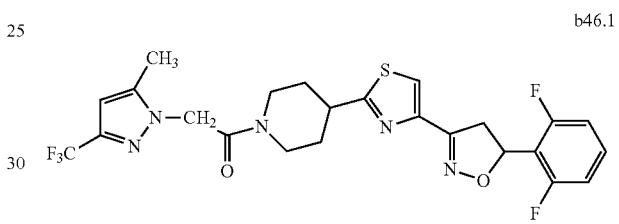

b46.1

(b46.2),

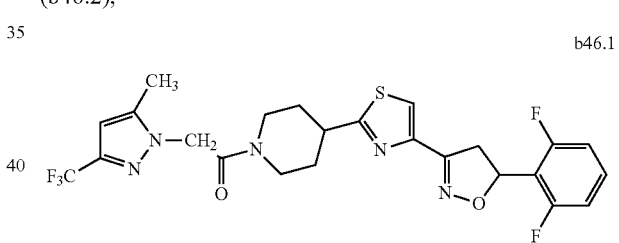

b46.1 wherein $R^{b1}$ is

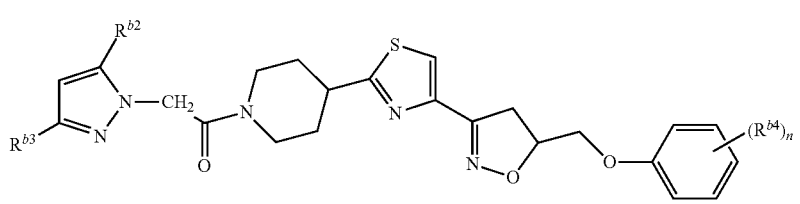

b46.3 and (b46.3)

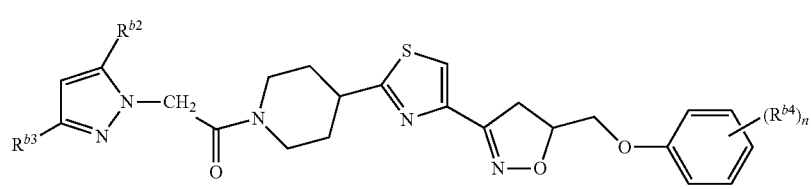

b46.3 wherein $R^{b2}$ is $CH_3$, $CF_3$ or $CHF_2$; $R^{b3}$ is $CH_3$, $CF_3$ or $CHF_2$; $R^{b4}$ is halogen or cyano; and n is 0, 1, 2 or 3.

Embodiment B51

The composition described in Embodiment B3 wherein component (b) includes at least one compound selected from (b46) fungicides other than fungicides of component (a) and components (b1)) through (b45), such as (b46.4)

b46.4 wherein $R^{b5}$ is —$CH_2OC(O)CH(CH_3)_2$, —$C(O)CH_3$, —$CH_2OC(O)CH_3$, —$C(O)OCH_2CH(CH_3)_2$ or Embodiment B52

The composition described in Embodiment B3 wherein component (b) includes at least one compound selected from (b46) fungicides other than fungicides of component (a) and components (b1)) through (b45), such as (b46.5)

b46.5

Embodiment B53

The composition described in Embodiment B3 wherein component (b) includes at least one compound selected from (b46) fungicides other than fungicides of component (a) and components (b1)) through (b45), such as (b46.6)

b46.6

Embodiment B54

The composition described in Embodiment B3 wherein component (b) includes at least one compound selected from (b46) fungicides other than fungicides of component (a) and components (b1)) through (b45), such as (b46.7)

b46.7 wherein $R^{b6}$ is H or F; and $R^{b7}$ is —$CF_2CHFCF_3$ or —$CF_2CF_2H$.

Embodiment B55

The composition described in Embodiment B3 wherein component (b) includes at least one compound selected from (b46) fungicides other than fungicides of component (a) and components (b1)) through (b45), such as (b46.8)

46.8 wherein
$R^{b8}$ is halogen, $C_1$-$C_4$ alkoxy or $C_2$-$C_4$ alkynyl;
$R^{b9}$ is H, halogen or $C_1$-$C_4$ alkyl;
$R^{b10}$ is $C_1$-$C_{12}$ alkyl, $C_1$-$C_{12}$ haloalkyl, $C_1$-$C_{12}$ alkoxy, $C_2$-$C_{12}$ alkoxyalkyl, $C_2$-$C_{12}$ alkenyl, $C_2$-$C_{12}$ alkynyl, $C_4$-$C_{12}$ alkoxyalkenyl, $C_4$-$C_{12}$ alkoxyalkynyl, $C_1$-$C_{12}$ alkylthio or $C_2$-$C_{12}$ alkylthioalkyl;
$R^{b11}$ is methyl or —$Y^{b13}$—$R^{b12}$;
$R^{b12}$ is $C_1$-$C_2$ alkyl; and
$Y^{b13}$ is $CH_2$, O or S.

Embodiment B56

The composition of Embodiment B55 wherein component (b) includes at least one fungicidal compound selected from the group consisting of (b46.8a) 2-[(3-bromo-6-quinolinyl)oxy]-N-(1,1-dimethyl-2-butyn-1-yl)-2-(methylthio)acetamide, (b46.8b) 2-[(3-ethynyl-6-quinolinyl)oxy]-N-[1-(hydroxymethyl)-1-methyl-2-propyn-1-yl]-2-(methylthio)acetamide, (b46.8c) N-(1,1-dimethyl-2-butyn-1-yl)-2-[(3-ethynyl-6-quinolinyl)oxy]-2-(methylthio)acetamide, (b46.8d) 2-[(3-bromo-8-methyl-6-quinolinyl)oxy]-N-(1,1-dimethyl-2-propyn-1-yl)-2-(methylthio)acetamide and (b46.8e) 2-[(3-bromo-6-quinolinyl)oxy]-N-(1,1-dimethylethyl)butanamide.

Embodiment B57

The composition of Embodiment B3 wherein component (b) includes at least one fungicidal compound selected from the group consisting of (b46.9)

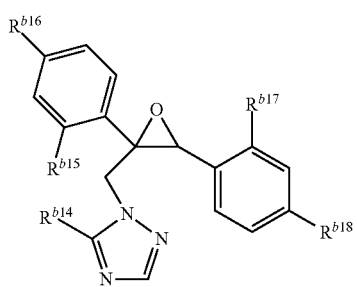

b46.9 wherein $R^{b14}$ is H, —SH, $C_1$-$C_6$ alkylthio, $C_1$-$C_6$ alkenylthio, $C_1$-$C_6$ alkynylthio or $C_4$-$C_7$ cycloalkylalkylthio; and $R^{b15}$, $R^{b16}$, $R^{b17}$ and $R^{b18}$ are each independently H or halogen; provided that (i) at least one of $R^{b15}$, $R^{b16}$, $R^{b17}$ and $R^{b18}$ is other than H.

Embodiment B58

The composition of Embodiment B57 wherein component (b) includes at least one fungicidal compound selected from the group consisting of (b46.9a) 1-[[(2S,3R)-3-(2-chlorophenyl)-2-(2,4-difluorophenyl)-2-oxiranyl]methyl]-1H-1,2,4-triazole, (b46.9b) 2-[[(2S,3R)-3-(2-chlorophenyl)-2-(2,4-difluorophenyl)-2-oxiranyl]methyl]-1,2-dihydro-3H-1,2,4-triazole-3-thione and (b46.9c) 1-[[(2S,3R)-3-(2-chlorophenyl)-2-(2,4-difluorophenyl)-2-oxiranyl]methyl]-5-(2-propen-1-ylthio)-1H-1,2,4-triazole.

Embodiment B59

The composition of Embodiment B3 wherein component (b) includes at least one fungicidal compound selected from the group consisting of (b46.10)

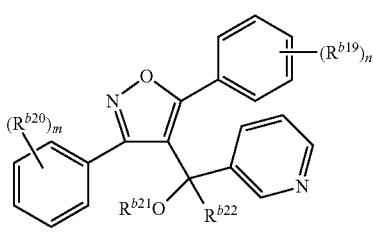

b46.10 wherein $R^{b19}$ and $R^{b20}$ are each independently halogen; $R^{b21}$ is H, $CH_3$, CHO or $C(O)CH_3$; $R^{b22}$ is H; or $R^{b21}$ and $R^{b22}$ are taken together as $CH_2$; and n and m are each independently 1 or 2.

Embodiment B60

The composition of Embodiment B59 wherein component (b) includes at least one fungicidal compound selected from the group consisting of (b46.10a) α-[3-(4-chloro-2-fluorophenyl)-5-(2,4-difluorophenyl)-4-isoxazolyl]-3-pyridinemethanol, (b46.10b) (αS)-[3-(4-chloro-2-fluorophenyl)-5-(2,4-difluorophenyl)-4-isoxazolyl]-3-pyridinemethanol, (b46.10c) (αR)-[3-(4-chloro-2-fluorophenyl)-5-(2,4-difluorophenyl)-4-isoxazolyl]-3-pyridinemethanol and (b46.10d) 3-[2-[3-(4-chloro-2-fluorophenyl)-5-(2,4-difluorophenyl)-4-isoxazolyl]-2-oxiranyl]pyridine.

Embodiment B61

The composition described in Embodiment B3 wherein component (b) includes at least one fungicidal compound (fungicide) selected from the group consisting of azoxystrobin, kresoxim-methyl, trifloxystrobin, pyraclostrobin, pyraoxystrobin, pyrametostrobin, picoxystrobin, dimoxystrobin, metominostrobin/fenominostrobin, carbendazim, chlorothalonil, quinoxyfen, metrafenone, pyriofenone, cyflufenamid, fenpropidin, fenpropimorph, bromuconazole, cyproconazole, difenoconazole, epoxiconazole, fenbuconazole, flusilazole, hexaconazole, ipconazole, metconazole, myclobutanil, penconazole, propiconazole, proquinazid, prothioconazole, tebuconazole, triticonazole, famoxadone, prochloraz, penthiopyrad and boscalid (nicobifen).

Embodiment B62

The composition of Embodiment B3 wherein component (b) includes at least one compound selected from the group consisting of azoxystrobin, kresoxim-methyl, trifloxystrobin, pyraclostrobin, pyrametostrobin, pyraoxystrobin, picoxystrobin, dimoxystrobin, metominostrobin-/fenominostrobin, quinoxyfen, metrafenone, pyriofenone, cyflufenamid, fenpropidin, fenpropimorph, cyproconazole, difenoconazole, epoxiconazole, flusilazole, metconazole, myclobutanil, propiconazole, proquinazid, prothioconazole, tebuconazole, triticonazole, famoxadone and penthiopyrad.

Embodiment B63

A composition comprising components (a) and (b) described in the Summary of the Invention or any one of Embodiments 1 through 62 further comprising (c) least one additional compound or agent that is biologically active.

Embodiment B64

The composition described in Embodiment 63 wherein component (c) comprises at least one fungicidal compound selected from the group consisting of:
(c1) methyl benzimidazole carbamate (MBC) fungicides;
(c2) dicarboximide fungicides;
(c3) demethylation inhibitor (DMI) fungicides;
(c4) phenylamide fungicides;
(c5) amine/morpholine fungicides;
(c6) phospholipid biosynthesis inhibitor fungicides;
(c7) carboxamide fungicides;

(c8) hydroxy(2-amino-)pyrimidine fungicides;
(c9) anilinopyrimidine fungicides;
(c10) N-phenyl carbamate fungicides;
(c11) quinone outside inhibitor (QoI) fungicides;
(c12) phenylpyrrole fungicides;
(c13) quinoline fungicides;
(c14) lipid peroxidation inhibitor fungicides;
(c15) melanin biosynthesis inhibitors-reductase (MBI-R) fungicides;
(c16) melanin biosynthesis inhibitors-dehydratase (MBI-D) fungicides;
(c17) hydroxyanilide fungicides;
(c18) squalene-epoxidase inhibitor fungicides;
(c19) polyoxin fungicides;
(c20) phenylurea fungicides;
(c21) quinone inside inhibitor (QiI) fungicides;
(c22) benzamide fungicides;
(c23) enopyranuronic acid antibiotic fungicides;
(c24) hexopyranosyl antibiotic fungicides;
(c25) glucopyranosyl antibiotic: protein synthesis fungicides;
(c26) glucopyranosyl antibiotic: trehalase and inositol biosynthesis fungicides;
(c27) cyanoacetamideoxime fungicides;
(c28) carbamate fungicides;
(c29) oxidative phosphorylation uncoupling fungicides;
(c30) organo tin fungicides;
(c31) carboxylic acid fungicides;
(c32) heteroaromatic fungicides;
(c33) phosphonate fungicides;
(c34) phthalamic acid fungicides;
(c35) benzotriazine fungicides;
(c36) benzene-sulfonamide fungicides;
(c37) pyridazinone fungicides;
(c38) thiophene-carboxamide fungicides;
(c39) pyrimidinamide fungicides;
(c40) carboxylic acid amide (CAA) fungicides;
(c41) tetracycline antibiotic fungicides;
(c42) thiocarbamate fungicides;
(c43) benzamide fungicides;
(c44) host plant defense induction fungicides;
(c45) multi-site contact activity fungicides;
(c46) fungicides other than fungicides of component (a) and components (c1) through (c45); and
salts of compounds of (c1) through (c46).

Embodiment C1

A compound of Formula 22 described in the Summary of the Invention.

Embodiment C2

A compound of Embodiment C1 wherein $R^1$ is F or Cl.

Embodiment C3

A compound of Embodiment C2 wherein $R^1$ is Cl.

Embodiment C4

A compound of Embodiment C2 wherein $R^1$ is F.

Embodiment C5

A compound of Embodiment C1 wherein $R^2$ is F, Cl or Br.

Embodiment C6

A compound of Embodiment C5 wherein $R^2$ is Cl or Br.

Embodiment C7

A compound of Embodiment C5 wherein $R^2$ is F.

Embodiment C8

A compound of Embodiment C5 wherein $R^2$ is Cl.

Embodiment C9

A compound of Embodiment C5 wherein $R^2$ is Br.

Embodiment C10

A compound of Embodiment C1 wherein $R^3$ is Cl or Br.

Embodiment C11

A compound of Embodiment C10 wherein $R^3$ is Cl.

Embodiment C12

A compound of Embodiment C10 wherein $R^3$ is Br.

Embodiment C13

A compound of Embodiment C1 wherein $R^3$ is F.

Embodiment C14

A compound of Embodiment C1 wherein M is Na.

Embodiment C15

A compound of Embodiment C1 wherein M is K.

Embodiment D1

A compound of Formula 18 described in the Summary of the Invention.

Embodiment D2

A compound of Embodiment D1 wherein $R^1$ is F or Cl.

Embodiment D3

A compound of Embodiment D2 wherein $R^1$ is Cl.

Embodiment D4

A compound of Embodiment D2 wherein $R^1$ is F.

Embodiment D5

A compound of Embodiment D1 wherein $R^2$ is F, Cl or Br.

Embodiment D6

A compound of Embodiment D5 wherein $R^2$ is Cl or Br.

Embodiment D7

A compound of Embodiment D5 wherein $R^2$ is F.

Embodiment D8

A compound of Embodiment D5 wherein $R^2$ is Cl.

Embodiment D9

A compound of Embodiment D5 wherein $R^2$ is Br.

Embodiment D10

A compound of Embodiment D1 wherein $R^3$ is Cl or Br.

Embodiment D11

A compound of Embodiment D10 wherein $R^3$ is Cl.

Embodiment D12

A compound of Embodiment D10 wherein $R^3$ is Br.

Embodiment D13

A compound of Embodiment D1 wherein $R^3$ is F.

Embodiment D14

A compound of Embodiment D1 wherein $R^{32}$ is H, $CH_3$ or $CH_2CH_3$.

Embodiment D15

A compound of Embodiment D14 wherein $R^{32}$ is H or $CH_3$.

Embodiment D16

A compound of Embodiment D15 wherein $R^{32}$ is H.

Embodiment D17

A compound of Embodiment D15 wherein $R^{32}$ is $CH_3$.

Embodiment E1

A compound of Formula 20 described in the Summary of the Invention.

Embodiment E2

A compound of Embodiment E1 wherein $R^1$ is F, Cl or Br
Embodiment E3. A compound of Embodiment E1 wherein $R^1$ is other than Cl or Br.

Embodiment E4

A compound of Embodiment E1 wherein $R^1$ is F.

Embodiment E5

A compound of Embodiment E1 wherein $R^2$ is F, Cl or Br.

Embodiment E6

A compound of Embodiment E5 wherein $R^2$ is F.

Embodiment E7

A compound of Embodiment E5 wherein $R^2$ is Cl.

Embodiment E8

A compound of Embodiment E5 wherein $R^2$ is Br.

Embodiment E9

A compound of Embodiment E1 wherein $R^1$ is Cl and $R^2$ is Cl.

Embodiments of this invention, including Embodiments A1-A13, B1-B64, C1-C15, D1-D17 and E1-E9 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments A1-A13, B1-B64, C1-C15, D1-D17 and E1-E9 above as well as any other embodiments described herein, and any combination thereof, pertain to the compositions and methods of the present invention.

Combinations of Embodiments A1-A13, B1-B64, C1-C15, D1-D17 and E1-E9 above as well as any other embodiments described herein are illustrated by:

Embodiment 1

A compound of Formula 1 wherein
$R^1$ is F or Cl; and
$R^2$ is F, Cl or Br.

Embodiment 2

A compound of Embodiment 1 wherein
$R^1$ is F; and
$R^2$ is Cl or Br.

Embodiment 3

A compound of Embodiment 2 wherein
$R^2$ is Br; and
$R^3$ is Cl or Br.

Specific embodiments include compounds of Formula 1 selected from the group consisting of:
N-(2-bromo-6-fluoro-4-methylphenyl)-4-(2-chloro-4-fluorophenyl)-1,3-dimethyl-1H-pyrazol-5-amine, (i.e. Compound 1)
4-(2-chloro-4-fluorophenyl)-N-(2-chloro-4-methylphenyl)-1,3-dimethyl-1H-pyrazol-5-amine, (i.e. Compound 2)
N-(2-bromo-4-methylphenyl)-4-(2-chloro-4-fluorophenyl)-1,3-dimethyl-1H-pyrazol-5-amine, (i.e. Compound 3)
4-(2-bromo-4-fluorophenyl)-N-(2-chloro-4-methylphenyl)-1,3-dimethyl-1H-pyrazol-5-amine, (i.e. Compound 4)
4-(2-bromo-4-fluorophenyl)-N-(2-bromo-4-methylphenyl)-1,3-dimethyl-1H-pyrazol-5-amine, (i.e. Compound 5)
4-(2-chloro-4-fluorophenyl)-N-(2-fluoro-4-methylphenyl)-1,3-dimethyl-1H-pyrazol-5-amine, (i.e. Compound 6)
N-(2-bromo-6-fluoro-4-methylphenyl)-4-(2-bromo-4-fluorophenyl)-1,3-dimethyl-1H-pyrazol-5-amine, (i.e. Compound 7)
N-(2-bromo-6-fluoro-4-methylphenyl)-4-(2,4-difluorophenyl)-1,3-dimethyl-1H-pyrazol-5-amine, (i.e. Compound 8)
N-(2,6-difluoro-4-methylphenyl)-4-(2,4-difluorophenyl)-1,3-dimethyl-1H-pyrazol-5-amine, (i.e. Compound 9)
4-(2-chloro-4-fluorophenyl)-N-(2,6-difluoro-4-methylphenyl)-1,3-dimethyl-1H-pyrazol-5-amine, (i.e. Compound 10)

4-(2-bromo-4-fluorophenyl)-N-(2-chloro-6-fluoro-4-methylphenyl)-1,3-dimethyl-1H-pyrazol-5-amine, (i.e. Compound 11)

N-(2-chloro-6-fluoro-4-methylphenyl)-4-(2-chloro-4-fluorophenyl)-1,3-dimethyl-1H-pyrazol-5-amine, (i.e. Compound 12)

4-(2-chloro-4-fluorophenyl)-N-(2,6-dichloro-4-methylphenyl)-1,3-dimethyl-1H-pyrazol-5-amine, (i.e. Compound 13)

4-(2-bromo-4-fluorophenyl)-N-(2,6-difluoro-4-methylphenyl)-1,3-dimethyl-1H-pyrazol-5-amine, (i.e. Compound 14)

4-(2-bromo-4-fluorophenyl)-N-(2,6-dichloro-4-methylphenyl)-1,3-dimethyl-1H-pyrazol-5-amine (i.e. Compound 15) and N-(2,6-dichloro-4-methylphenyl)-4-(2,4-difluorophenyl)-1,3-dimethyl-1H-pyrazol-5-amine (i.e. Compound 16).

Also, specific embodiments include compounds of Formula 1 selected from the group consisting of: N-(2-bromo-6-fluoro-4-methylphenyl)-4-(2-chloro-4-fluorophenyl)-1,3-dimethyl-1H-pyrazol-5-amine, (i.e. Compound 1), 4-(2-chloro-4-fluorophenyl)-N-(2-chloro-4-methylphenyl)-1,3-dimethyl-1H-pyrazol-5-amine, (i.e. Compound 2), N-(2-bromo-4-methylphenyl)-4-(2-chloro-4-fluorophenyl)-1,3-dimethyl-1H-pyrazol-5-amine, (i.e. Compound 3), 4-(2-bromo-4-fluorophenyl)-N-(2-chloro-4-methylphenyl)-1,3-dimethyl-1H-pyrazol-5-amine, (i.e. Compound 4), 4-(2-bromo-4-fluorophenyl)-N-(2-bromo-4-methylphenyl)-1,3-dimethyl-1H-pyrazol-5-amine, (i.e. Compound 5), 4-(2-chloro-4-fluorophenyl)-N-(2-fluoro-4-methylphenyl)-1,3-dimethyl-1H-pyrazol-5-amine, (i.e. Compound 6), N-(2-bromo-6-fluoro-4-methylphenyl)-4-(2-bromo-4-fluorophenyl)-1,3-dimethyl-1H-pyrazol-5-amine, (i.e. Compound 7), N-(2-bromo-6-fluoro-4-methylphenyl)-4-(2,4-difluorophenyl)-1,3-dimethyl-1H-pyrazol-5-amine, (i.e. Compound 8), N-(2,6-difluoro-4-methylphenyl)-4-(2,4-difluorophenyl)-1,3-dimethyl-1H-pyrazol-5-amine, (i.e. Compound 9), 4-(2-chloro-4-fluorophenyl)-N-(2,6-difluoro-4-methylphenyl)-1,3-dimethyl-1H-pyrazol-5-amine, (i.e. Compound 10), 4-(2-bromo-4-fluorophenyl)-N-(2-chloro-6-fluoro-4-methylphenyl)-1,3-dimethyl-1H-pyrazol-5-amine, (i.e. Compound 11) and N-(2-chloro-6-fluoro-4-methylphenyl)-4-(2-chloro-4-fluorophenyl)-1,3-dimethyl-1H-pyrazol-5-amine, (i.e. Compound 12).

This invention provides a fungicidal composition comprising a compound of Formula 1 (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all stereoisomers, N-oxides, and salts thereof). Of note as embodiment of such methods are methods comprising applying a fungicidally effective amount of a compound corresponding to any of the compound embodiments describe above. Of particular notes are embodiment where the compounds are applied as compositions of this invention.

One or more of the following methods and variations as described in Schemes 1-18 can be used to prepare the compounds of Formula 1. As described in the Summary of the Invention, an aspect of the present invention is directed at a composition comprising as component (a) at least one compound selected from Formula 1, N-oxides, and salts thereof. One or more of the following methods and variations as described in Schemes 1-18 can be used to prepare the compounds of Formula 1. The definitions of $R^1$, $R^2$ and $R^3$, M and $R^{32}$ in the compounds of Formulae 1-23 below are as defined above in the Summary of the Invention unless otherwise noted. Formulae 7a, 7b and 7c are various subsets of Formula 7; Formula 11a is a subset of Formula 11; and Formula 18a is a tautomeric subset of Formula 18. Substituents for each subset formula are as defined for its parent formula unless otherwise noted.

As shown in Scheme 1, compounds of Formula 1 can be prepared by the reaction of the corresponding compounds of Formula 2 containing a group at the aniline 4-position such as bromine, iodine or trifluoromethanesulfonate with reagents such as 2,4,6-trimethylboroxine, tetramethylstannane or potassium trifluromethylborate in the presence of a catalyst such as [1,1'-bis(diphenylphosphino)ferrocene]palladium(II) chloride dichloromethane adduct, preferably in the presence of an organic or inorganic base such as 1,8-diazabicyclo[5.4.0]undec-7-ene, cesium carbonate or potassium hydroxide, and in a solvent such as N,N-dimethylformamide (DMF), tetrahydrofuran (THF), 1,4-dioxane, ethanol, toluene or water. Compounds of Formula 2 can be prepared by the methods described in WO 2010/101973 and WO 2012/031061. The method of Scheme 1 is illustrated by Step A of synthesis Example 4.

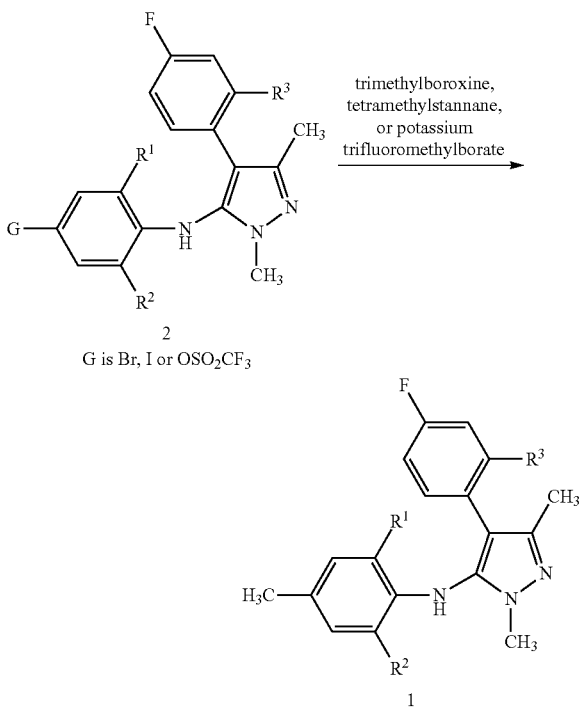

Scheme 1

As shown in Scheme 2, compounds of Formula 1 can be prepared by the reaction of 1H-pyrazole compounds of Formula 3 with various methylating agents (e.g., Formula 4), such as iodomethane, methyl sulfonates (e.g., methyl mesylate (OMs) or tosylate (OTs)) or trimethyl phosphate, preferably in the presence of an organic or inorganic base such as 1,8-diazabicyclo[5.4.0]undec-7-ene, potassium carbonate or potassium hydroxide, and in a solvent such as N,N-dimethylformamide (DMF), tetrahydrofuran (THF), toluene or water.

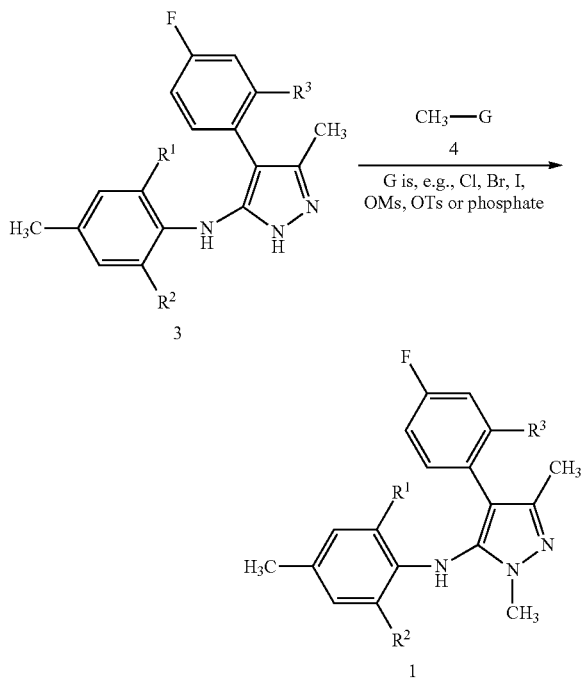

Scheme 2

As is shown in Scheme 3, compounds of Formula 1 can be prepared by the reaction of compounds of Formula 5 with aromatic compounds of Formula 6 containing a leaving group G (e.g., halogen or (halo)alkylsulfonate), optionally in the presence of a metal catalyst, and generally in the presence of a base and a polar aprotic solvent such as N,N-dimethylformamide or dimethyl sulfoxide. For example, compounds of Formula 6 wherein the benzene ring contains electron-withdrawing substituents react by direct displacement of the leaving group G from the ring to provide compounds of Formula 1. Compounds of Formula 6 are commercially available or their preparation is known in the art.

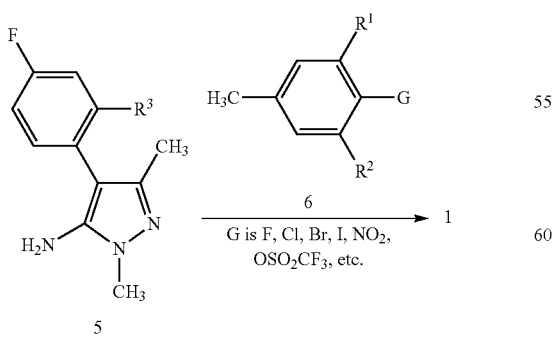

Scheme 3

For reactions according to the method of Scheme 3 of a compound of Formula 5 with a compound of Formula 6 wherein the aromatic ring lacks sufficiently electron-withdrawing substituents, or to improve reaction rate, yield or product purity, the use of a metal catalyst (e.g., metal or metal salt) in amounts ranging from catalytic up to superstoichiometric can facilitate the desired reaction. Typically for these conditions, G is Br or I or a sulfonate such as $OS(O)_2CF_3$ or $OS(O)_2(CF_2)_3CF_3$. For example, copper salt complexes (e.g., CuI with N,N-dimethylethylenediamine, proline or bipyridyl), palladium complexes (e.g., tris-(dibenzylideneacetone)dipalladium(0)) or palladium salts (e.g., palladium acetate) with ligands such as 4,5-bis(diphenylphosphino)-9,9-dimethylxanthene (i.e. "Xantphos"), 2-dicyclohexylphosphino-2',4',6'-triisopropylbiphenyl (i.e. "Xphos") or 2,2'-bis(diphenyl-phosphino)-1,1'-binaphthalene (i.e. "BINAP"), in the presence of a base such as potassium carbonate, cesium carbonate, sodium phenoxide or sodium tert-butoxide, in a solvent such as N,N-dimethylformamide, 1,2-dimethoxyethane, dimethyl sulfoxide, 1,4-dioxane or toluene, optionally mixed with alcohols such as ethanol, can be used. Alternatively as illustrated in Scheme 4, compounds of Formula 1 can be prepared by reaction of compounds of Formula 7 (i.e. 5-bromopyrazoles or other pyrazoles substituted at the 5-position with a leaving group) with compounds of Formula 8 under metal-catalyzed conditions similar to those described above for Scheme 3. Compounds of Formula 8 are commercially available or alternatively, can be prepared by the method illustrated in Step A of synthesis Example 1 or by methods known in the art. Of note is a compound of Formula 8 wherein $R^1$ is F and $R^2$ is Br; or wherein $R^1$ is F and $R^2$ is F; or wherein $R^1$ is F and $R^2$ is Cl.

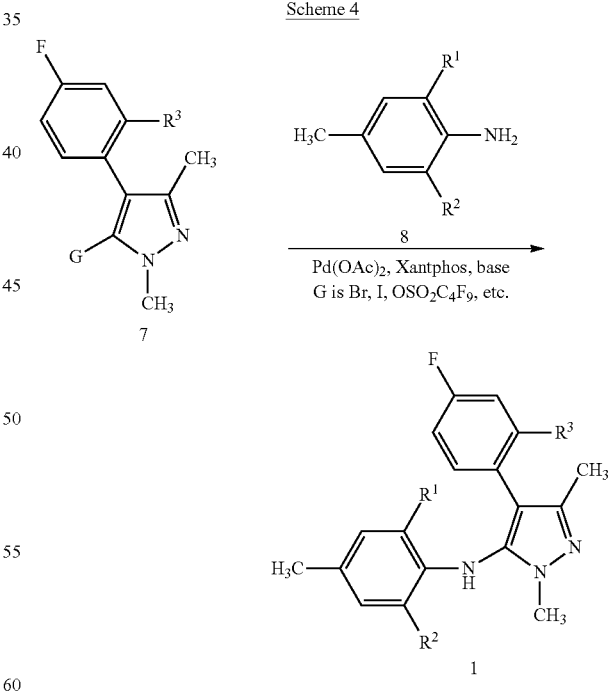

Scheme 4

As shown in Scheme 5, compounds of Formula 7a wherein G is Br or I can be prepared by reaction of 5-aminopyrazoles of Formula 5 under diazotization conditions either in the presence of, or followed by combination with, copper salts containing bromide or iodide. For example, addition of tert-butyl nitrite to a solution of a 5-aminopyrazole of Formula 5 in the presence of CuBr$_2$ in a solvent such as acetonitrile provides the corresponding 5-bromopyrazole of Formula 7a. Likewise, a 5-aminopyrazole of Formula 5 can be converted to a diazonium salt and then to a corresponding 5-halopyrazole of Formula 7a by treatment with sodium nitrite in solvents such as water, acetic acid or trifluoroacetic acid, in the presence of a mineral acid typically containing the same halide atom (such as aqueous HI solution for G being I), followed by treatment with the corresponding copper(I) or copper(II) salt according to general procedures well known to those skilled in the art.

Scheme 5

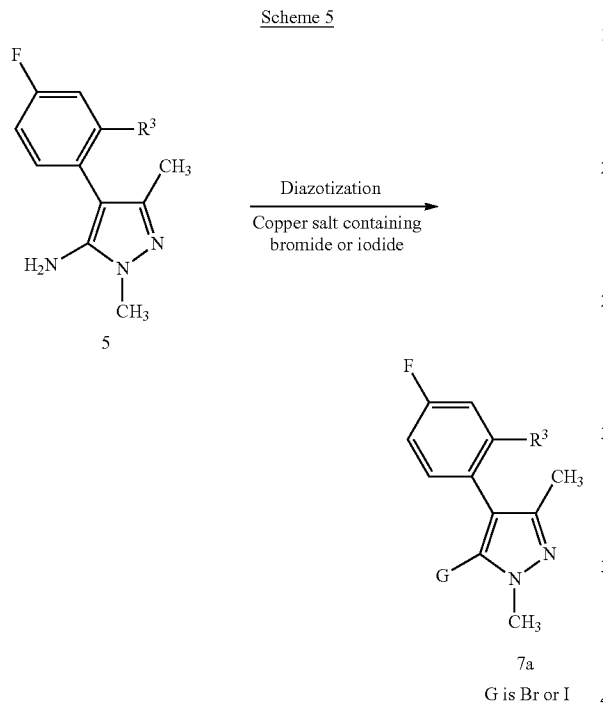

7a
G is Br or I

As shown in Scheme 6, 5-bromopyrazoles of Formula 7b (i.e. Formula 7 wherein G is Br) can be prepared by reacting 5-hydroxypyrazoles of Formula 9 with phosphorus tribromide as described in *Tetrahedron Lett.* 2000, 41(24), 4713.

Scheme 6

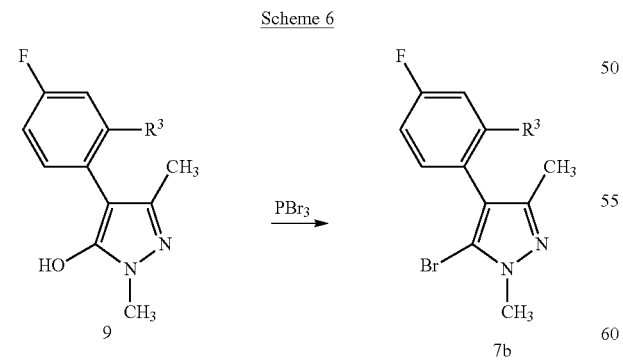

As shown in Scheme 7, 5-hydroxypyrazoles of Formula 9 can also be used to prepare 5-fluoroalkylsulfonyl (e.g., 5-trifluoromethanesulfonyl, 5-nonafluorobutylsulfonyl) pyrazoles of Formula 7c (i.e. Formula 7 wherein G is fluoroalkylsulfonyl) as described in *Synlett* 2004, 5, 795.

Scheme 7

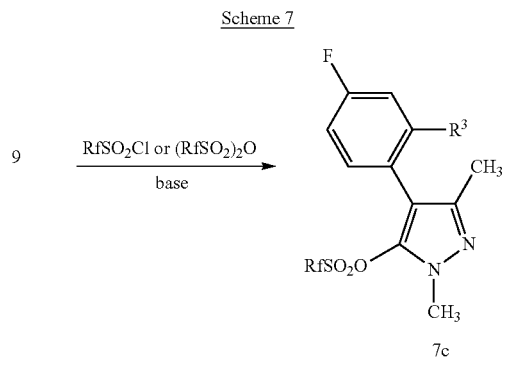

wherein Rf is fluoroalkyl such as CF$_3$ or (CF$_2$)$_2$CF$_3$

As shown in Scheme 8, compounds of Formula 1 can be prepared by reaction of 4-bromo or iodo pyrazoles of Formula 10 with organometallic compounds of Formula 11 under transition-metal-catalyzed cross-coupling reaction conditions. Reaction of a 4-bromo or iodo pyrazole of Formula 10 with a boronic acid, trialkyltin, zinc or organomagnesium reagent of Formula 11 in the presence of a palladium or nickel catalyst having appropriate ligands (e.g., triphenylphosphine (PPh$_3$), dibenzylideneacetone (dba), dicyclohexyl(2',6'-dimethoxy[1,1'-biphenyl]-2-yl)phosphine (SPhos)) and a base, if needed, affords the corresponding compound of Formula 1. For example, a substituted aryl boronic acid or derivative (e.g., Formula 11 wherein M is B(OH)$_2$, B(OC(CH$_3$)$_2$C(CH$_3$)$_2$O)) or B(O-i-Pr)$_3$) reacts with a 4-bromo- or 4-iodopyrazole of Formula 10 in the presence of dichlorobis(triphenylphosphine) palladium(II) and aqueous base such as sodium carbonate or potassium hydroxide, in solvents such as 1,4-dioxane, 1,2-dimethoxyethane, toluene or ethyl alcohol, or under anhydrous conditions with a ligand such as phosphine oxide or phosphite ligand (e.g., diphenylphosphine oxide) and potassium fluoride in a solvent such as 1,4-dioxane (see *Angewandte Chemie, International Edition* 2008, 47(25), 4695-4698) to provide the corresponding compound of Formula 1.

Scheme 8

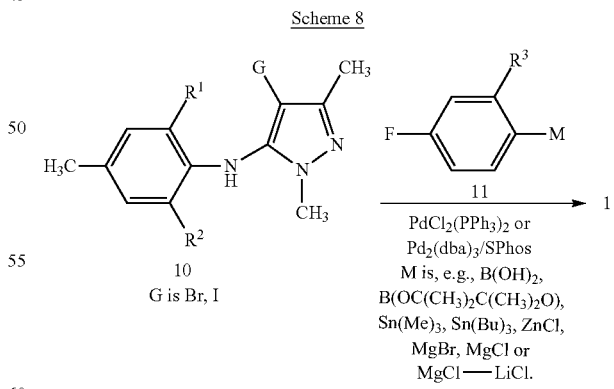

As illustrated in Scheme 9, compounds of Formula 5 can be prepared by reacting compounds of Formula 12 with compounds of Formula 11a (e.g., compounds of Formula 11 wherein M is B(OH)$_2$) using transition-metal-catalyzed cross-coupling reaction conditions as described for the method of Scheme 8.

Scheme 9

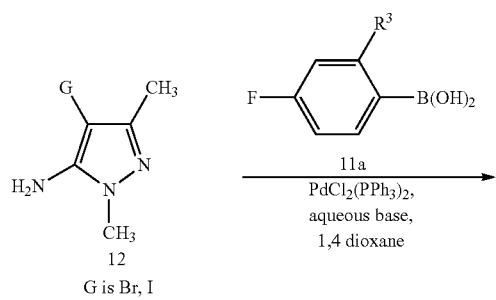

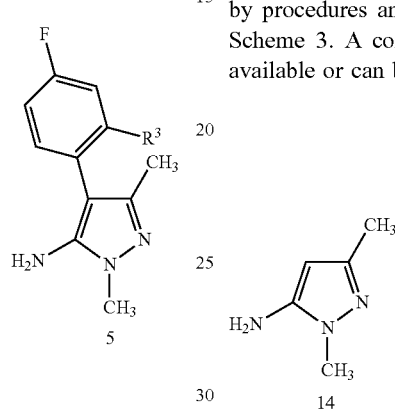

As illustrated in Scheme 10, pyrazoles of Formula 10 wherein G is Br or I are readily prepared by the reaction of pyrazoles unsubstituted at the 4-position (Formula 13) with halogenating reagents such as bromine, sodium bromite, N-bromosuccinimide (NBS) or N-iodosuccinimide (NIS), in solvents such as acetic acid, acetonitrile, N,N-dimethylformamide, N,N-dimethylacetamide or 1,4-dioxane, or a mixture of water with the aforementioned solvents, at temperatures ranging from ambient to the boiling point of the solvent.

Scheme 10

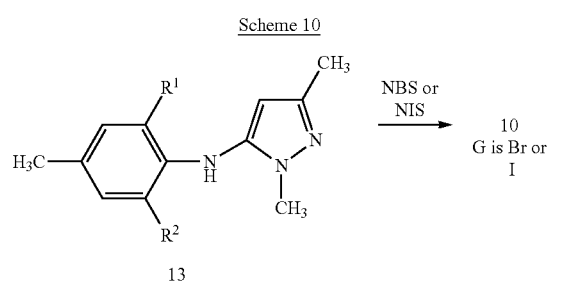

As illustrated in Scheme 11, using reaction conditions similar to those for the method of Scheme 10, the pyrazole of Formula 14 can be converted into intermediates of Formula 12 which are useful for preparing compounds of Formula 5 as depicted in Scheme 9. The compound of Formula 14 not only can be prepared by methods known in the art, but is also commercially available.

Scheme 11

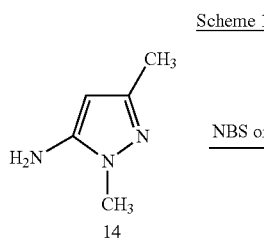

As shown in Scheme 12, compounds of Formula 13 can be prepared from corresponding compounds of Formula 14 by procedures analogous to those used for the method of Scheme 3. A compound of Formula 14 is commercially available or can be prepared by methods known in the art.

Scheme 12

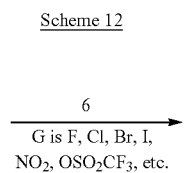

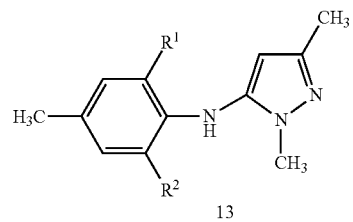

General methods useful for preparing 5-aminopyrazoles of Formula 5 are well known in the art; see, for example, *Journal für Praktische Chemie* (Leipzig) 1911, 83, 171 and *J. Am. Chem. Soc.* 1954, 76, 501. Such a method is illustrated in Scheme 13.

Scheme 13

Similarly, general methods useful for preparing 5-hydroxypyrazoles of Formula 9 are well known in the art; see, for example, *Annalen der Chemie* 1924, 436, 88. Such a method is illustrated in Scheme 14.

Scheme 14

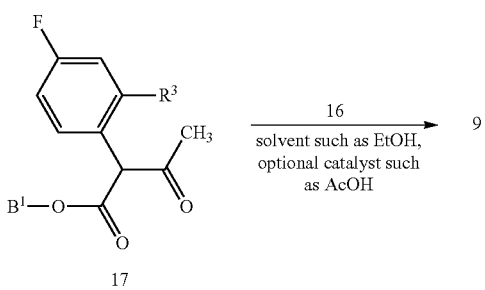

B¹ is alkyl, aryl, benzyl, etc.

Scheme 16

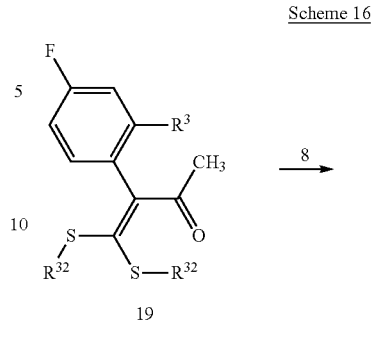

wherein $R^{32}$ is H, $CH_3$, $CH_2CH_3$ or $(CH_2)_2CH_3$

As shown in Scheme 15, compounds of Formula 1 can be prepared by condensing compounds of Formula 18 with methylhydrazine (Formula 16) in a solvent such as ethanol, methanol or toluene and optionally in the presence of an acid or base catalyst such as acetic acid, piperidine or sodium methoxide, at temperatures known in the art. The method of Scheme 15 is illustrated by Step A of synthesis Example 3.

Scheme 15

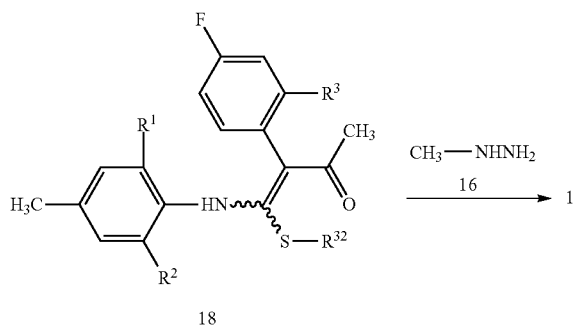

wherein $R^{32}$ is $CH_3$, $CH_2CH_3$ or $(CH_2)_2CH_3$)

In a manner analogous to the method of Scheme 15, compounds of Formula 3 can be similarly prepared by condensing compounds of Formula 18 with hydrazine. This method is described in *Chemistry of Heterocyclic Compounds* 2005, 41(1), 105-110.

As shown in Scheme 16, compounds of Formula 18 (wherein $R^{32}$ is H or lower alkyl such as $CH_3$, $CH_2CH_3$ or $(CH_2)_2CH_3$) can be prepared by reaction of corresponding ketene dithioacetal compounds of Formula 19 with compounds of Formula 8 optionally in the presence of a base, such as sodium hydride or ethylmagnesium chloride, in solvents such as toluene, tetrahydrofuran or dimethoxymethane, at temperatures ranging from −10° C. to the boiling point of the solvent. See, for example, *J. Heterocycl. Chem.* 1975, 12(1), 139. Additional methods useful for preparing compounds of Formula 18 are known in the art.

As shown in Scheme 17, compounds of Formula 18 wherein $R^{32}$ is lower alkyl (e.g., methyl, ethyl or n-propyl) and Formula 18a (i.e. tautomer of Formula 18 wherein $R^{32}$ is H) can be prepared starting by condensation reaction of corresponding isothiocyanate compounds of Formula 20 with arylacetone compounds of Formula 21 to give intermediate compounds of Formula 22, which are salts of the thioamides of Formula 20a. The intermediate compounds of Formula 22 can either be used in situ or isolated before further conversion. Bases useful for preparing compounds of Formula 22 include hydrides, alkoxides, hydroxides or carbonates of sodium or potassium, such as sodium hydride, potassium tert-butoxide, sodium ethoxide, potassium hydroxide, sodium hydroxide or potassium carbonate. Amine bases (e.g., triethylamine or N,N-diisopropylethylamine) can also be used to effect the condensation of the compounds of Formulae 20 and 21. A variety of solvents are useful, such as tetrahydrofuran, ether, toluene, N,N-dimethylformamide, alcohols (e.g., ethanol), esters (e.g., ethyl acetate or isopropyl acetate), or mixtures thereof. Solvents are chosen for compatibility with the base selected, as is well-known in the art. Reaction temperatures can range from −78° C. to the boiling point of the solvent. One useful mixture of base and solvent is potassium tert-butoxide in tetrahydrofuran, to which at −70 to 0° C. is added a solution of an isothiocyanate of Formula 20 and a carbonyl compound of Formula 21, which are either combined into one solution, or added separately, preferably by addition of the carbonyl compound followed by addition of the isothiocyanate. The salt compound of Formula 22 can be acidified to form the ketothioamide compound of Formula 18a or alkylated with $R^{32}X^1$ (Formula 23) wherein $R^{32}$ is lower alkyl (e.g., methyl, ethyl or n-propyl) and $X^1$ is a nucleofuge (i.e. a nucleophilic reaction leaving group such as Br, I, $OS(O)_2CH_3$) to form the corresponding compound of Formula 18. This general method is known in the chemical literature; see, for example, *Zhurnal Organicheskoi Khimii* 1982, 18(12), 2501. The method of Scheme 17 to prepare a non-isolated intermediate compound of Formula 18 wherein $R^{32}$ is methyl is illustrated by synthesis Example 3.

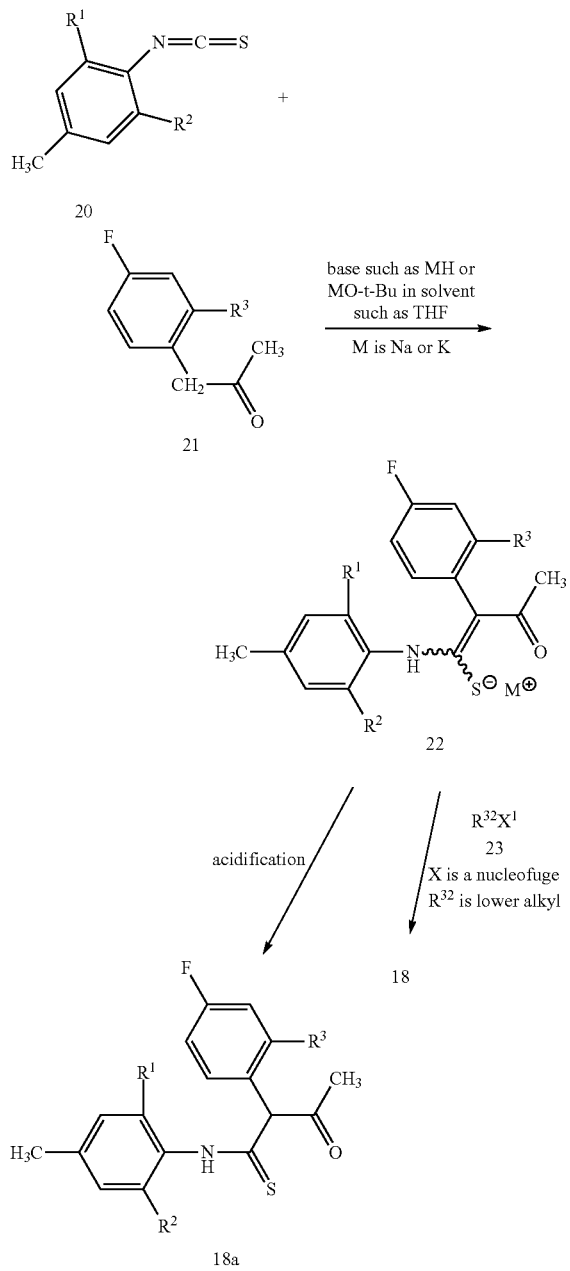

Ketothioamides of Formula 18a can also be prepared by allowing the corresponding ketoamides to react with sulfurizing agents such as Lawesson's reagent or $P_2S_5$; see, for example, *Helv. Chim. Act.* 1998, 81(7), 1207. Compounds of Formula 20 can be prepared from the corresponding anilines of Formula 8 as shown in Scheme 18 under conditions such as treatment with thiophosgene, optionally in the presence of a base such as potassium carbonate or diisopropylethylamine in such solvents or mixtures of solvents as chloroform, tetrahydrofuran, toluene, or water, at temperatures from $-10°$ C. to the boiling point of the solvent, according to general procedures known in the literature. This reaction can also be performed by contacting a compound of Formula 8 with thiocarbonyldiimidazole (TCDI) or carbon disulfide, under conditions well-known in the art. The method of Scheme 18 is illustrated by Step A of synthesis Example 2.

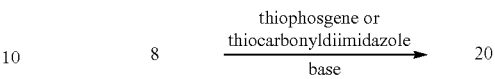

$$8 \xrightarrow[\text{base}]{\text{thiophosgene or thiocarbonyldiimidazole}} 20$$

An additional method for preaparing a compound of Formula 20 from a compound of Formula 8 using 1,1'-thiocarbonyldi-2,2'-pyridone can be found in *J.O.C.* 1986, 51(13), 2613. Alternatively, a compound of Formula 20 can be prepared from the corresponding thiourea (i.e. a compound of Formula 6 wherein G is —NHC(=S)NH$_2$) by heating in a high boiling solvent such as toluene, xylenes or o-dichlorobenzene as described similarly in *Org. Syn.* 1936, 36, 56.

It is recognized by one skilled in the art that various functional groups can be converted into others to provide different compounds of Formula 1. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1.

The above reactions can also in many cases be performed in alternate sequence, such as the preparation of 1H pyrazoles for use in the reaction in Scheme 3 by reactions illustrated later for the general preparation of substituted pyrazoles.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in CDCl$_3$ in ppm downfield from tetramethylsilane; "s" means singlet, "d" means doublet, "m" means multiplet and "br s" means broad singlet.

EXAMPLE 1

Step A: Preparation of
2-chloro-6-fluoro-4-methylbenzeneamine (Note 4-2)

To a solution of 4-bromo-2-chloro-6-fluorobenzeneamine (1.00 g, 4.45 mmol) in 1,4-dioxane (15 mL) was added water (1.5 mL) and cesium carbonate (2.90 g, 8.91 mmol), then the mixture was sparged with nitrogen subsurface. After ~5 min, 2,4,6-trimethylboroxine (3.14 mL, 22.3 mmol) and [1,1'-bis)diphenylphosphino)ferrocene]dichloropalladium(II) complex with CH$_2$Cl$_2$ (0.36 g, 0.44 mmol) were added, and the mixture was stirred under a nitrogen atmosphere and heated at reflux for 3 h. The reaction mixture was allowed to cool to ambient temperature, and then filtered through a 1-cm pad of Celite® diatomaceous filter aid with ethyl acetate elution (~50 mL). The filtrate was concentrated and then purified by medium-pressure chromatography on silica gel with a solvent gradient of 5% to 100% ethyl acetate in hexanes to obtain 0.23 g of the title compound as clear, light-brown oil.
$^1$H NMR δ 6.87 (s, 1H), 6.74 (d, 1H), 3.90 (br s, 2H) 2.22 (s, 3H).

EXAMPLE 2

Step A: Preparation of
1-chloro-3-fluoro-2-isothiocyanato-5-methylbenzene
(Note 3-2)

2-Chloro-6-fluoro-4-methylbenzeneamine (i.e. the product from Example 1) (0.23 g, 1.44 mmol) was dissolved in dichloromethane (5 mL). Potassium carbonate (0.24 g, 1.7 mmol) and water (5 mL) were added and the resulting mixture was stirred at ambient temperature while a solution of thiophosgene (0.125 mL, 1.5 mmol) in dichloromethane (5 mL) was added dropwise over ~5 min. This mixture was stirred vigorously at ambient temperature for 16 h, then additional potassium carbonate (0.60 g, 4.3 mmol), water (2 mL), thiophosgene (0.083 mL) and dichloromethane (2 mL), were added, and stirring was continued for 16 h. The reaction mixture was partitioned, the organic layer removed, and the aqueous phase extracted once with dichloromethane (~20 mL). The organic phases were combined, dried over magnesium sulfate, and concentrated under reduced pressure. The resultant residue was purified by medium-pressure chromatography on silica gel with hexanes to obtain 0.050 g of the title compound as a clear, colorless oil.
$^1$H NMR δ 7.02 (s, 1H), 6.85 (d, 1H), 2.33 (s, 3H).

EXAMPLE 3

Step A: Preparation of N-(2-bromo-6-fluoro-4-methylphenyl)-4-(2-chloro-4-fluorophenyl)-1,3-dimethyl-1H-pyrazol-5-amine (Compound 1)

Potassium tert-butoxide (1.0 M solution in tetrahydrofuran, 4.46 mL, 4.46 mmol) was combined with anhydrous tetrahydrofuran (12 mL) and cooled under a nitrogen atmosphere to ~0° C. (ice/acetone bath). A solution of 2-chloro-4-fluorophenylacetone (0.75 g, 4.06 mmol) in anhydrous tetrahydrofuran (~2 mL) was added dropwise, and the reaction mixture was stirred a further 1 h at ~0° C. The reaction mixture was then cooled to −20° C. in a dry ice/acetone bath. A solution of 1-bromo-3-fluoro-2-isothiocyanato-5-methylbenzene (1.00 g, 4.06 mmol) in anhydrous tetrahydrofuran (~2 mL) was added dropwise, and this mixture was stirred at −20 to −3° C. for about 30 min. A solution of iodomethane (0.30 mL, 4.8 mmol) in anhydrous tetrahydrofuran was added dropwise, and the resultant suspension was stirred for about 5 min. A solution of methylhydrazine (1.52 mL, 28.4 mmol) and glacial acetic acid (0.7 mL, 12 mmol) in methanol (7 mL) was added and this mixture was heated at reflux for about 2 h and then allowed to cool to ambient temperature and stirred for 16 h. Aqueous sodium hydroxide solution (3N, 16 mL) was added to the reaction mixture, and then volatiles were removed under reduced pressure. The resulting residue was partitioned between about 50 mL ethyl acetate and about 50 mL water. The aqueous phase was extracted twice with about 25 mL ethyl acetate, and the combined organic phases were washed with brine solution, dried over magnesium sulfate, and concentrated. The resulting yellow oil was purified by medium-pressure chromatography on silica gel with a solvent gradient of 5% to 100% ethyl acetate in hexanes to obtain the desired product as a yellow solid. Trituration with 20% ethyl acetate/hexanes afforded 0.49 g of the title compound as an off-white solid (m.p. 136-137° C.). An additional crop of (0.155 g) was obtained as a tan solid (m.p. 132-133° C.).
$^1$H NMR δ 7.03-7.08 (m, 2H), 6.94 (s, 1H), 6.82 (m, 1H), 6.61 (m, 1H), 5.32 (br s, 1H), 3.77 (s, 3H), 2.17 (s, 3H), 2.10 (s, 3H); MS 428 (AP+).

EXAMPLE 4

Step A: Preparation of N-(2,6-difluoro-4-methylphenyl)-4-(2,4-difluorophenyl)-1,3-dimethyl-1H-pyrazol-5-amine (Compound 9)

To a mixture of N-(4-bromo-2,6-difluorophenyl)-4-(2,4-difluorophenyl)-1,3-dimethyl-1H-pyrazol-5-amine (i.e. as prepared in WO 2010/101973 A1) (0.12 g, 0.29 mmol) in 1,4-dioxane (2 mL) was added cesium carbonate (0.19 g, 0.57 mmol), water (4 drops) and [1,1'-bis)diphenylphosphino)ferrocene]dichloropalladium(II) complex with CH$_2$Cl$_2$ (0.024 g, 0.29 mmol), and this mixture was sparged with nitrogen subsurface for 5 min. 2,4,6-Trimethylboroxine (0.203 mL, 1.44 mmol) was added, and the mixture was stirred under a nitrogen atmosphere and heated at reflux for 3 h. After cooling to ambient temperature, the reaction mixture was filtered through a 1-cm pad of Celite® diatomaceaous filter aid, eluting with ethyl acetate (~25 mL). The filtrate was concentrated and then purified by medium-pressure chromatography on silica gel with a solvent gradient of 5% to 100% ethyl acetate in hexanes to obtain 0.081 g of the title compound as a white solid (m.p. 156-158° C.).
$^1$H NMR δ 7.07 (m, 1H), 6.70-6.79 (m, 2H), 6.52 (m, 2H), 5.12 (br s, NH), 3.75 (s, 3H), 2.18 (s, 3H), 2.17 (s, 3H); MS 350 (AP+).

By the procedures described herein together with methods known in the art, the following compounds of Tables 1 to 4 can be prepared. The "Note" column in Tables 1b, 2, 3 and 4 reference physical property data (e.g., $^1$H NMR spectra) for representative compounds.

As described for Scheme 17, compounds of Formula 18 including Formula 18a (Formula 18 tautomer wherein R$^{32}$ is H) are useful process intermediates for preparing compounds of Formula 1, which are also useful as component (a) in the present composition. Illustrative of compounds of Formulae 18 and 18a are those specifically disclosed in Table 1a and 1b below.

TABLE 1a

[Structure: Tautomeric equilibrium between compound 18a (thioamide form with H₃C-phenyl-NH-C(=S)- group attached to CH(4-F-phenyl-R³)-C(=O)-CH₃) and compound 18 (enol/thiol form with S—R³²).]

| R¹ | R² | R³ | R¹ | R² | R³ |
|----|----|----|----|----|----|
| F  | H  | Cl | F  | F  | Cl |
| Cl | H  | Cl | Cl | F  | Cl |
| Br | H  | Cl | Br | F  | Cl |
| F  | H  | Br | F  | F  | Br |
| Cl | H  | Br | Cl | F  | Br |
| Br | H  | Br | Br | F  | Br |

R³² is H.

TABLE 1b

[Structure 18: H₃C-phenyl(R¹,R²)-HN-C(S—R³²)=C(4-F-phenyl-R³)-C(=O)-CH₃]

| R¹ | R² | R³ | Note | R¹ | R² | R³ | Note |
|----|----|----|------|----|----|----|------|
| \multicolumn{8}{c}{R³² is CH₃} ||||||||

| R¹ | R² | R³ | Note | R¹ | R² | R³ | Note |
|----|----|----|------|----|----|----|------|
| F  | H  | Cl | 1b-1 | F  | F  | Cl |      |
| Cl | H  | Cl |      | Cl | F  | Cl |      |
| Br | H  | Cl |      | Br | F  | Cl |      |
| F  | H  | Br |      | F  | F  | Br |      |
| Cl | H  | Br |      | Cl | F  | Br |      |
| Br | H  | Br |      | Br | F  | Br |      |

R³² is CH₂CH₃

| R¹ | R² | R³ | R¹ | R² | R³ |
|----|----|----|----|----|----|
| F  | H  | Cl | F  | F  | Cl |
| Cl | H  | Cl | Cl | F  | Cl |
| Br | H  | Cl | Br | F  | Cl |
| F  | H  | Br | F  | F  | Br |
| Cl | H  | Br | Cl | F  | Br |
| Br | H  | Br | Br | F  | Br |

R³² is (CH₂)₂CH₃

| R¹ | R² | R³ | R¹ | R² | R³ |
|----|----|----|----|----|----|
| F  | H  | Cl | F  | F  | Cl |
| Cl | H  | Cl | Cl | F  | Cl |
| Br | H  | Cl | Br | F  | Cl |
| F  | H  | Br | F  | F  | Br |
| Cl | H  | Br | Cl | F  | Br |
| Br | H  | Br | Br | F  | Br |

Note 1b-1:
$^1$H NMR (CDCl₃) δ 12.78 (s, 1H), 7.42 (m, 1H), 7.21-7.32 (m, 2H), 7.03 (m, 1H), 6.94 (m, 1H), 6.93 (s, 1H), 2.34 (s, 3H), 1.88 (s, 3H), 1.86 (s, 3H).

TABLE 2

[Structure 22: H₃C-phenyl(R¹,R²)-N(H)-C(S⁻ M⁺)=C(4-F-phenyl-R³)-C(=O)-CH₃]

M is Na.

| R¹ | R² | R³ | Note | R¹ | R² | R³ | Note |
|----|----|----|------|----|----|----|------|
| F  | H  | Cl |      | F  | F  | Cl |      |
| Cl | H  | Cl |      | Cl | F  | Cl |      |
| Br | H  | Cl |      | Br | F  | Cl |      |
| F  | H  | Br |      | F  | F  | Br |      |
| Cl | H  | Br |      | Cl | F  | Br |      |
| Br | H  | Br |      | Br | F  | Br |      |

M is K.

| R¹ | R² | R³ | R¹ | R² | R³ |
|----|----|----|----|----|----|
| F  | H  | Cl | F  | F  | Cl |
| Cl | H  | Cl | Cl | F  | Cl |
| Br | H  | Cl | Br | F  | Cl |
| F  | H  | Br | F  | F  | Br |
| Cl | H  | Br | Cl | F  | Br |
| Br | H  | Br | Br | F  | Br |

As described for Scheme 17, compounds of Formula 20 are useful process intermediates for preparing compounds of Formulae 18 and 18a as intermediates for preparing compounds of Formula 1, which also are useful as component (a) in the present composition. An example of a compound of Formula 20 is specifically disclosed in Step A of Example 2. An additional example is found in Table 3.

TABLE 3

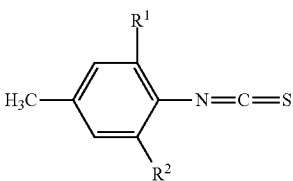

| R$^1$ | R$^2$ | Note | R$^1$ | R$^2$ | Note |
|---|---|---|---|---|---|
| F | H | | F | F | 3-1 |
| Cl | H | | Cl | F | 3-2 |
| Br | H | | Br | F | |
| | | | Cl | Cl | 3-3 |

Note 3-1:
$^1$H NMR (CDCl$_3$) δ 6.76 (d, 2H), 2.34 (s, 3H).
Note 3-2:
See Step A of synthesis Example 2 for $^1$H NMR spectrum.
Note 3-3:
M.P. = 65-67 ° C.

As described for Scheme 4, compounds of Formula 8 are useful process intermediates for preparing compounds of Formula 1 which are also useful as component (a) in the present composition. Additionally, compounds of Formula 8 are useful process intermediates for preparing compounds of Formulae 18 (as shown in Scheme 17) or of Formulae 20 (as shown in Scheme 18) as intermediates for preparing compounds of Formula 1, which are useful as component (a) in the present composition. An example of a compound of Formula 8 is specifically disclosed in Step A of Example 1. Illustrative of compounds of Formula 8 are those specifically disclosed in Table 4.

TABLE 4

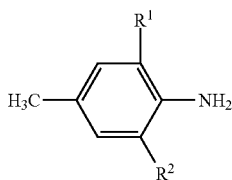

8

| R$^1$ | R$^2$ | Note | R$^1$ | R$^2$ | Note |
|---|---|---|---|---|---|
| F | H | | F | F | 4-1 |
| Cl | H | | Cl | F | 4-2 |
| Br | H | | Br | F | |
| | | | Cl | Cl | |

Note 4-1:
$^1$H NMR (CDCl$_3$) δ 6.63 (d, 2H), 3.55 (br s, 2H), 2.28 (s, 3H)
Note 4-2:
See Step A of synthesis Example 1 for $^1$H NMR spectrum.

Remarkably, 4-methyl aniline-pyrazole compounds of Formula 1 have now been discovered to have significantly improved pharmacokinetic properties compared to corresponding compounds wherein the aniline has a halogen (i.e. F, Cl or Br) substituent at the 4-position. In particular in vertebrate animals, compounds of Formula 1 compared to para-halo substituted analogs have been found to have a significantly diminished distribution into fat, thereby reducing the possibility of bioaccumulation. Furthermore, in addition to having more favorable pharmacokinetic properties in vertebrate animals, 4-methyl anilino-pyrazole compounds of Formula 1 have been discovered to retain remarkably high activity against plant fungal diseases, such as caused by Septoria tritici. Because of their extraordinarily desirable biological profile, compounds of Formula 1 are remarkably useful as component (a) in combination with fungicidal compounds of component (b) and optionally other biologically active compounds or agents as component (c) in the present compositions. Moreover, process intermediates useful for preparing compounds of Formula 1, such as compounds of Formulae 18, 20 and 22 are correspondingly particularly useful.

The pharmacokinetic properties of compounds of Formula 1 can be measured using a wide variety of assay protocols known in the science of pharmacology. In one illustrative method involving a single oral dose, three male and three female rats receive a single dose of a test substance via oral gavage. Approximately 0.25 mL of blood is collected via tail vein immediately prior to dosing, and then at 0.25, 0.5, 1, 2, 4, 8, 12, 24 h and every 24 h thereafter until sacrifice. At sacrifice, fat is also collected to determine the fat:plasma ratio at sacrifice. Blood is collected into tubes that contain ethylenediaminetetracetic acid (EDTA) and centrifuged at 2500×g in order to separate plasma from blood cells. The plasma is then extracted by protein precipitation using, for example, acetonitrile and a protein precipitation plate (e.g., Strata Impact Protein Precipitation Plate, part number CEO-7565 of Phenomenex, Torrance, Calif., U.S.A.) following directions provided for the plate. Alternatively, the plasma is extracted just with acetonitrile, vortexed (i.e. mixed using a vortex mixer), and centrifuged to pellet the proteins. After removal of the proteins, the plasma is analyzed for parent compound and/or metabolites by liquid chromatography-mass spectrometry (LC/MS). The fat is homogenized and extracted by an organic solvent such as acetonitrile. The extract is then analyzed for parent compound and/or metabolites by LC/MS. The plasma pharmacokinetic data is then analyzed using nonlinear modeling software (e.g., WinNonlin™ from Pharsight, Cary, N.C., U.S.A.) to determine half-life of the administered compound in plasma, the time after administration when the maximum plasma concentration is reached ($T_{max}$), the maximum plasma concentration ($C_{max}$) and the area under the plasma concentration curve (AUC). As analysis of fat requires rat sacrifice, fat data is obtained at single time points (i.e. the time of rat sacrifice). However, by using multiple rats sacrificed after different intervals from time of dosing, such parameters as $C_{max}$ for fat are determined. Using the above described method, Compound 1 identified in Index Table A are found to have a significantly diminished distribution into fat compared to corresponding compounds wherein R$^2$ is other than halogen.

Table A1 lists specific combinations of a Component (b) compound with Compound 1 as Component (a) illustrative of the mixtures, compositions and methods of the present invention. (Compound numbers refer to compounds in Index Table A.) The second column of Table A1 lists ranges of Typical Weight Ratios the specific Component (b) compound (e.g., acibenzolar-S-methyl in the first line) is applied with Compound 1 as Component (a). The third and fourth columns of Table A1 list ranges of weight ratios for rates at which the Component (a) compound is More Typically and Most Typically applied to a field-grown crop relative to Component (b). The fifth column of Table A1 lists an Illustrative Weight Ratio for rates at which the Component (a) compound is typically applied to a field-grown crop relative to Component (b). Thus, for example, the first line of Table A1 specifically discloses the combination of acibenzolar-S-methyl with Compound 1 is typically applied in a weight ratio of acibenzolar-S-methyl to Compound 1 of between 2:1 and 1:180 (i.e. Component (b):Component (a) to Component (b):Component (a)); more typically applied in a weight ratio of acibenzolar-S-methyl to Compound 1 of between 1:1 and 1:60; most typically applied in a weight ratio of acibenzolar-S-methyl to Compound 1 of between 1:1 and 1:18; and is applied in a weight ratio of acibenzolar-S-methyl to Compound 1 of 1:4. The remaining lines of Table A1 are to be construed similarly.

TABLE A1

| Component (b) | Typical Weight Ratio | More Typical Weight Ratio | Most Typical Weight Ratio | Illustrative Weight Ratio |
|---|---|---|---|---|
| acibenzolar-S-methyl | 2:1 to 1:180 | 1:1 to 1:60 | 1:1 to 1:18 | 1:4 |
| Aldimorph | 30:1 to 1:3 | 10:1 to 1:1 | 7:1 to 1:1 | 3:1 |
| Ametoctradin | 9:1 to 1:18 | 3:1 to 1:6 | 3:1 to 1:3 | 1:1 |
| Amisulbrom | 6:1 to 1:18 | 2:1 to 1:6 | 1:1 to 1:6 | 1:2 |
| Anilazine | 90:1 to 2:1 | 30:1 to 4:1 | 22:1 to 4:1 | 8:1 |
| Azaconazole | 7:1 to 1:18 | 2:1 to 1:6 | 2:1 to 1:4 | 2:1 |
| Azoxystrobin | 9:1 to 1:12 | 3:1 to 1:4 | 3:1 to 1:3 | 1:1 |
| Benalaxyl | 4:1 to 1:18 | 1:1 to 1:6 | 1:1 to 1:6 | 1:2 |
| benalaxyl-M | 4:1 to 1:36 | 1:1 to 1:12 | 1:1 to 1:8 | 1:3 |
| Benodanil | 18:1 to 1:6 | 6:1 to 1:2 | 4:1 to 1:2 | 2:1 |
| Benomyl | 45:1 to 1:4 | 15:1 to 1:1 | 11:1 to 1:1 | 4:1 |
| benthiavalicarb or benthiavalicarb-isopropyl | 2:1 to 1:36 | 1:1 to 1:12 | 1:1 to 1:12 | 1:4 |
| bethoxazin | 150:1 to 1:36 | 50:1 to 1:12 | 15:1 to 2:1 | 5:1 |
| binapacryl | 150:1 to 1:36 | 50:1 to 1:12 | 15:1 to 2:1 | 5:1 |
| biphenyl | 150:1 to 1:36 | 50:1 to 1:12 | 15:1 to 2:1 | 5:1 |
| bitertanol | 15:1 to 1:5 | 5:1 to 1:2 | 3:1 to 1:2 | 2:1 |
| bixafen | 12:1 to 1:9 | 4:1 to 1:3 | 2:1 to 1:3 | 1:1 |
| blasticidin-S | 3:1 to 1:90 | 1:1 to 1:30 | 1:4 to 1:30 | 1:12 |
| boscalid | 18:1 to 1:6 | 6:1 to 1:2 | 4:1 to 1:2 | 2:1 |
| bromuconazole | 15:1 to 1:9 | 5:1 to 1:3 | 3:1 to 1:3 | 2:1 |
| bupirimate | 3:1 to 1:90 | 1:1 to 1:30 | 1:3 to 1:30 | 1:10 |
| captafol | 90:1 to 1:4 | 30:1 to 1:2 | 15:1 to 2:1 | 5:1 |
| captan | 90:1 to 1:4 | 30:1 to 1:2 | 15:1 to 2:1 | 5:1 |
| carbendazim | 45:1 to 1:4 | 15:1 to 1:2 | 11:1 to 2:1 | 4:1 |
| carboxin | 18:1 to 1:6 | 6:1 to 1:2 | 4:1 to 1:2 | 2:1 |
| carpropamid | 15:1 to 1:9 | 5:1 to 1:3 | 3:1 to 1:3 | 1:1 |
| chloroneb | 300:1 to 2:1 | 100:1 to 4:1 | 100:1 to 14:1 | 35:1 |
| chlorothalonil | 90:1 to 1:4 | 30:1 to 1:2 | 15:1 to 2:1 | 5:1 |
| chlozolinate | 45:1 to 1:2 | 15:1 to 2:1 | 11:1 to 2:1 | 4:1 |
| clotrimazole | 15:1 to 1:9 | 5:1 to 1:3 | 3:1 to 1:3 | 1:1 |
| copper salts such as Bordeaux mixture (tribasic copper sulfate), copper oxychloride, copper sulfate and copper hydroxide | 450:1 to 1:1 | 150:1 to 4:1 | 45:1 to 5:1 | 15:1 |
| cyazofamid | 4:1 to 1:18 | 1:1 to 1:6 | 1:1 to 1:6 | 1:2 |
| cyflufenamid | 1:1 to 1:90 | 1:2 to 1:30 | 1:2 to 1:24 | 1:6 |
| cymoxanil | 6:1 to 1:18 | 2:1 to 1:6 | 1:1 to 1:5 | 1:2 |
| cyproconazole | 8:1 to 1:18 | 6:1 to 1:6 | 5:1 to 1:6 | 2:1 |
| cyprodinil | 22:1 to 1:9 | 7:1 to 1:3 | 4:1 to 1:2 | 2:1 |
| dichlofluanid | 150:1 to 1:36 | 50:1 to 1:12 | 15:1 to 2:1 | 5:1 |
| diclocymet | 150:1 to 1:36 | 50:1 to 1:12 | 15:1 to 2:1 | 5:1 |
| diclomezine | 15:1 to 1:9 | 5:1 to 1:3 | 3:1 to 1:3 | 1:1 |
| dicloran | 150:1 to 1:36 | 50:1 to 1:12 | 15:1 to 2:1 | 5:1 |
| diethofencarb | 22:1 to 1:9 | 7:1 to 1:3 | 7:1 to 1:2 | 2:1 |
| difenoconazole | 8:1 to 1:36 | 6:1 to 1:12 | 4:1 to 1:12 | 2:1 |
| diflumetorim | 150:1 to 1:36 | 50:1 to 1:12 | 15:1 to 2:1 | 5:1 |
| dimethirimol | 3:1 to 1:90 | 1:1 to 1:30 | 1:3 to 1:30 | 1:8 |
| dimethomorph | 9:1 to 1:6 | 3:1 to 1:2 | 3:1 to 1:2 | 1:1 |
| dimoxystrobin | 9:1 to 1:18 | 3:1 to 1:6 | 2:1 to 1:4 | 1:1 |
| diniconazole | 8:1 to 1:36 | 6:1 to 1:12 | 4:1 to 1:12 | 2:1 |
| diniconazole M | 8:1 to 1:36 | 6:1 to 1:12 | 4:1 to 1:12 | 2:1 |
| dinocap | 7:1 to 1:9 | 2:1 to 1:3 | 2:1 to 1:3 | 1:1 |
| dithianon | 15:1 to 1:4 | 5:1 to 1:2 | 5:1 to 1:2 | 2:1 |
| dodemorph | 30:1 to 1:3 | 10:1 to 1:1 | 7:1 to 1:1 | 3:1 |
| dodine | 30:1 to 1:2 | 10:1 to 2:1 | 10:1 to 2:1 | 4:1 |
| edifenphos | 30:1 to 1:9 | 10:1 to 1:3 | 3:1 to 1:3 | 1:1 |
| enestroburin | 9:1 to 1:18 | 3:1 to 1:6 | 2:1 to 1:4 | 1:1 |
| epoxiconazole | 8:1 to 1:36 | 6:1 to 1:12 | 4:1 to 1:12 | 2:1 |
| etaconazole | 8:1 to 1:36 | 6:1 to 1:12 | 4:1 to 1:12 | 2:1 |
| ethaboxam | 7:1 to 1:9 | 2:1 to 1:3 | 2:1 to 1:3 | 1:1 |
| ethirimol | 30:1 to 1:3 | 10:1 to 1:1 | 7:1 to 1:1 | 3:1 |
| etridiazole | 30:1 to 1:9 | 10:1 to 1:3 | 7:1 to 1:2 | 2:1 |
| famoxadone | 9:1 to 1:18 | 3:1 to 1:6 | 2:1 to 1:4 | 1:1 |
| fenamidone | 6:1 to 1:18 | 2:1 to 1:6 | 2:1 to 1:4 | 1:1 |
| fenarimol | 8:1 to 1:36 | 6:1 to 1:12 | 4:1 to 1:12 | 2:1 |
| fenbuconazole | 8:1 to 1:36 | 6:1 to 1:12 | 4:1 to 1:12 | 2:1 |
| fenfuram | 18:1 to 1:6 | 6:1 to 1:2 | 4:1 to 1:2 | 1:1 |
| fenhexamid | 30:1 to 1:2 | 10:1 to 2:1 | 10:1 to 2:1 | 4:1 |
| fenoxanil | 150:1 to 1:36 | 50:1 to 1:12 | 15:1 to 1:1 | 4:1 |
| fenpiclonil | 75:1 to 1:9 | 25:1 to 1:3 | 15:1 to 2:1 | 5:1 |

TABLE A1-continued

| Component (b) | Typical Weight Ratio | More Typical Weight Ratio | Most Typical Weight Ratio | Illustrative Weight Ratio |
|---|---|---|---|---|
| fenpropidin | 30:1 to 1:3 | 10:1 to 1:1 | 7:1 to 1:1 | 3:1 |
| fenpropimorph | 30:1 to 1:3 | 10:1 to 1:1 | 7:1 to 1:1 | 3:1 |
| fenpyrazamine | 100:1 to 1:100 | 10:1 to 1:10 | 3:1 to 1:3 | 1:1 |
| fentin salt such as the acetate, chloride or hydroxide | 15:1 to 1:9 | 5:1 to 1:3 | 3:1 to 1:3 | 1:1 |
| ferbam | 300:1 to 1:2 | 100:1 to 2:1 | 30:1 to 4:1 | 10:1 |
| ferimzone | 30:1 to 1:5 | 10:1 to 1:2 | 7:1 to 1:2 | 2:1 |
| fluazinam | 22:1 to 1:5 | 7:1 to 1:2 | 3:1 to 1:2 | 1:1 |
| fludioxonil | 7:1 to 1:12 | 2:1 to 1:4 | 2:1 to 1:4 | 1:1 |
| flumetover | 9:1 to 1:6 | 3:1 to 1:2 | 3:1 to 1:2 | 1:1 |
| flumorph | 9:1 to 1:18 | 3:1 to 1:6 | 3:1 to 1:3 | 1:1 |
| fluopicolide | 3:1 to 1:18 | 1:1 to 1:6 | 1:1 to 1:6 | 1:2 |
| fluopyram | 15:1 to 1:90 | 5:1 to 1:30 | 3:1 to 1:3 | 1:1 |
| fluoromide | 150:1 to 2:1 | 50:1 to 4:1 | 37:1 to 5:1 | 14:1 |
| fluoxastrobin | 4:1 to 1:18 | 1:1 to 1:6 | 1:1 to 1:6 | 1:2 |
| fluquinconazole | 8:1 to 1:36 | 6:1 to 1:12 | 4:1 to 1:12 | 2:1 |
| flusilazole | 15:1 to 1:9 | 5:1 to 1:3 | 3:1 to 1:3 | 2:1 |
| flusulfamide | 90:1 to 1:2 | 30:1 to 2:1 | 15:1 to 2:1 | 5:1 |
| flutianil | 7:1 to 1:36 | 2:1 to 1:12 | 1:1 to 1:6 | 1:2 |
| flutolanil | 18:1 to 1:6 | 6:1 to 1:2 | 4:1 to 1:2 | 1:1 |
| flutriafol | 8:1 to 1:36 | 6:1 to 1:12 | 4:1 to 1:12 | 2:1 |
| fluxapyroxad | 12:1 to 1:9 | 4:1 to 1:3 | 2:1 to 1:3 | 1:1 |
| folpet | 90:1 to 1:4 | 30:1 to 1:2 | 15:1 to 2:1 | 5:1 |
| fosetyl-aluminum | 225:1 to 2:1 | 75:1 to 5:1 | 30:1 to 5:1 | 12:1 |
| fuberidazole | 45:1 to 1:4 | 15:1 to 1:2 | 11:1 to 2:1 | 4:1 |
| furalaxyl | 15:1 to 1:45 | 5:1 to 1:15 | 1:1 to 1:6 | 1:2 |
| furametpyr | 150:1 to 1:36 | 50:1 to 1:12 | 15:1 to 2:1 | 5:1 |
| guazatine or iminoctadine | 150:1 to 1:36 | 50:1 to 1:12 | 15:1 to 2:1 | 5:1 |
| hexaconazole | 8:1 to 1:36 | 6:1 to 1:12 | 4:1 to 1:12 | 2:1 |
| hymexazol | 225:1 to 2:1 | 75:1 to 4:1 | 75:1 to 9:1 | 25:1 |
| imazalil | 15:1 to 1:36 | 5:1 to 1:12 | 3:1 to 1:5 | 2:1 |
| imibenconazole | 15:1 to 1:36 | 5:1 to 1:12 | 3:1 to 1:5 | 2:1 |
| iodocarb | 150:1 to 1:36 | 50:1 to 1:12 | 15:1 to 2:1 | 4:1 |
| ipconazole | 15:1 to 1:36 | 5:1 to 1:12 | 3:1 to 1:5 | 2:1 |
| iprobenfos | 150:1 to 1:36 | 50:1 to 1:12 | 15:1 to 2:1 | 5:1 |
| iprodione | 120:1 to 1:2 | 40:1 to 2:1 | 15:1 to 2:1 | 5:1 |
| iprovalicarb | 9:1 to 1:9 | 3:1 to 1:3 | 2:1 to 1:3 | 1:1 |
| isofetamid | 20:1 to 1:20 | 5:1 to 1:5 | 3:1 to 1:3 | 1:1 |
| isoprothiolane | 150:1 to 2:1 | 50:1 to 4:1 | 45:1 to 5:1 | 15:1 |
| isopyrazam | 12:1 to 1:9 | 4:1 to 1:3 | 2:1 to 1:3 | 1:1 |
| isotianil | 12:1 to 1:9 | 4:1 to 1:3 | 2:1 to 1:3 | 1:1 |
| kasugamycin | 7:1 to 1:90 | 2:1 to 1:30 | 1:2 to 1:24 | 1:7 |
| kresoxim-methyl | 7:1 to 1:18 | 2:1 to 1:6 | 2:1 to 1:4 | 1:1 |
| mancozeb | 180:1 to 1:3 | 60:1 to 2:1 | 22:1 to 3:1 | 7:1 |
| mandipropamid | 6:1 to 1:18 | 2:1 to 1:6 | 2:1 to 1:4 | 1:1 |
| maneb | 180:1 to 1:3 | 60:1 to 2:1 | 22:1 to 3:1 | 7:1 |
| mepanipyrim | 18:1 to 1:3 | 6:1 to 1:1 | 6:1 to 1:1 | 2:1 |
| mepronil | 7:1 to 1:36 | 2:1 to 1:12 | 1:1 to 1:6 | 1:2 |
| meptyldinocap | 7:1 to 1:9 | 2:1 to 1:3 | 2:1 to 1:3 | 1:1 |
| metalaxyl | 15:1 to 1:45 | 5:1 to 1:15 | 1:1 to 1:6 | 1:2 |
| metalaxyl-M | 7:1 to 1:90 | 2:1 to 1:30 | 1:1 to 1:12 | 1:4 |
| metconazole | 8:1 to 1:36 | 6:1 to 1:12 | 4:1 to 1:12 | 2:1 |
| methasulfocarb | 150:1 to 1:36 | 50:1 to 1:12 | 15:1 to 1:1 | 5:1 |
| metiram | 150:1 to 1:36 | 50:1 to 1:12 | 15:1 to 1:1 | 5:1 |
| metominostrobin | 9:1 to 1:12 | 3:1 to 1:4 | 3:1 to 1:3 | 1:1 |
| metrafenone | 6:1 to 1:12 | 2:1 to 1:4 | 2:1 to 1:4 | 1:1 |
| myclobutanil | 8:1 to 1:36 | 6:1 to 1:12 | 4:1 to 1:12 | 2:1 |
| naftifine | 150:1 to 1:36 | 50:1 to 1:12 | 15:1 to 2:1 | 5:1 |
| neo-asozin (ferric methanearsonate) | 150:1 to 1:36 | 50:1 to 1:12 | 15:1 to 2:1 | 5:1 |
| nuarimol | 15:1 to 1:9 | 5:1 to 1:3 | 3:1 to 1:3 | 2:1 |
| octhilinone | 150:1 to 1:36 | 50:1 to 1:12 | 15:1 to 1:1 | 4:1 |
| ofurace | 15:1 to 1:45 | 5:1 to 1:15 | 1:1 to 1:6 | 1:2 |
| orysastrobin | 9:1 to 1:12 | 3:1 to 1:4 | 3:1 to 1:3 | 1:1 |
| oxadixyl | 15:1 to 1:45 | 5:1 to 1:15 | 1:1 to 1:6 | 1:2 |
| oxolinic acid | 30:1 to 1:9 | 10:1 to 1:3 | 7:1 to 1:2 | 2:1 |
| oxpoconazole | 15:1 to 1:36 | 5:1 to 1:12 | 3:1 to 1:5 | 2:1 |
| oxycarboxin | 18:1 to 1:6 | 6:1 to 1:2 | 4:1 to 1:2 | 1:1 |
| oxytetracycline | 15:1 to 1:9 | 5:1 to 1:3 | 3:1 to 1:3 | 1:1 |
| pefurazoate | 150:1 to 1:36 | 50:1 to 1:12 | 15:1 to 2:1 | 5:1 |
| penconazole | 8:1 to 1:36 | 6:1 to 1:12 | 4:1 to 1:12 | 2:1 |
| pencycuron | 150:1 to 1:2 | 50:1 to 2:1 | 11:1 to 2:1 | 4:1 |
| penflufen | 12:1 to 1:9 | 4:1 to 1:3 | 2:1 to 1:3 | 1:1 |
| penthiopyrad | 12:1 to 1:9 | 4:1 to 1:3 | 2:1 to 1:3 | 1:1 |
| phosphorous acid and salts thereof | 150:1 to 1:36 | 50:1 to 1:12 | 15:1 to 2:1 | 6:1 |
| phthalide | 150:1 to 1:36 | 50:1 to 1:12 | 15:1 to 2:1 | 6:1 |

TABLE A1-continued

| Component (b) | Typical Weight Ratio | More Typical Weight Ratio | Most Typical Weight Ratio | Illustrative Weight Ratio |
|---|---|---|---|---|
| picoxystrobin | 7:1 to 1:18 | 2:1 to 1:6 | 1:1 to 1:5 | 1:2 |
| piperalin | 15:1 to 1:9 | 5:1 to 1:3 | 3:1 to 1:3 | 1:1 |
| polyoxin | 15:1 to 1:9 | 5:1 to 1:3 | 3:1 to 1:3 | 1:1 |
| probenazole | 8:1 to 1:36 | 6:1 to 1:12 | 4:1 to 1:12 | 2:1 |
| prochloraz | 22:1 to 1:4 | 7:1 to 1:1 | 7:1 to 1:2 | 2:1 |
| procymidone | 45:1 to 1:3 | 15:1 to 1:1 | 11:1 to 2:1 | 4:1 |
| propamocarb or propamocarb-hydrochloride | 30:1 to 1:2 | 10:1 to 2:1 | 10:1 to 2:1 | 4:1 |
| propiconazole | 8:1 to 1:36 | 6:1 to 1:12 | 4:1 to 1:12 | 2:1 |
| propineb | 45:1 to 1:2 | 15:1 to 2:1 | 11:1 to 2:1 | 4:1 |
| proquinazid | 3:1 to 1:36 | 1:1 to 1:12 | 1:1 to 1:12 | 1:3 |
| prothiocarb | 9:1 to 1:18 | 3:1 to 1:6 | 3:1 to 1:3 | 1:1 |
| prothioconazole | 8:1 to 1:36 | 6:1 to 1:12 | 4:1 to 1:12 | 2:1 |
| pyraclostrobin | 9:1 to 1:18 | 3:1 to 1:6 | 2:1 to 1:4 | 1:1 |
| pyrametostrobin | 9:1 to 1:18 | 3:1 to 1:6 | 2:1 to 1:4 | 1:1 |
| pyraoxystrobin | 9:1 to 1:18 | 3:1 to 1:6 | 2:1 to 1:4 | 1:1 |
| pyrazophos | 150:1 to 1:36 | 50:1 to 1:12 | 15:1 to 1:1 | 4:1 |
| pyribencarb | 15:1 to 1:6 | 5:1 to 1:2 | 4:1 to 1:2 | 1:1 |
| pyrifenox | 15:1 to 1:9 | 5:1 to 1:3 | 3:1 to 1:3 | 2:1 |
| pyrimethanil | 30:1 to 1:6 | 10:1 to 1:2 | 3:1 to 1:2 | 1:1 |
| pyriofenone | 6:1 to 1:12 | 2:1 to 1:4 | 2:1 to 1:4 | 1:1 |
| pyroquilon | 15:1 to 1:9 | 5:1 to 1:3 | 3:1 to 1:3 | 1:1 |
| pyrrolnitrin | 150:1 to 1:36 | 50:1 to 1:12 | 15:1 to 2:1 | 5:1 |
| quinconazole | 8:1 to 1:36 | 6:1 to 1:12 | 4:1 to 1:12 | 2:1 |
| quinomethionate | 150:1 to 1:36 | 50:1 to 1:12 | 15:1 to 2:1 | 5:1 |
| quinoxyfen | 4:1 to 1:18 | 1:1 to 1:6 | 1:1 to 1:6 | 1:2 |
| quintozene | 150:1 to 1:36 | 50:1 to 1:12 | 15:1 to 2:1 | 5:1 |
| silthiofam | 7:1 to 1:18 | 2:1 to 1:6 | 2:1 to 1:4 | 1:1 |
| simeconazole | 8:1 to 1:36 | 6:1 to 1:12 | 4:1 to 1:12 | 2:1 |
| spiroxamine | 22:1 to 1:4 | 7:1 to 1:2 | 5:1 to 1:2 | 2:1 |
| streptomycin | 15:1 to 1:9 | 5:1 to 1:3 | 3:1 to 1:3 | 1:1 |
| sulfur | 300:1 to 3:1 | 100:1 to 9:1 | 75:1 to 9:1 | 25:1 |
| tebuconazole | 8:1 to 1:36 | 6:1 to 1:12 | 4:1 to 1:12 | 2:1 |
| tebufloquin | 100:1 to 1:100 | 10:1 to 1:10 | 3:1 to 1:3 | 1:1 |
| tecloftalam | 150:1 to 1:36 | 50:1 to 1:12 | 15:1 to 2:1 | 5:1 |
| tecnazene | 150:1 to 1:36 | 50:1 to 1:12 | 15:1 to 2:1 | 5:1 |
| terbinafine | 150:1 to 1:36 | 50:1 to 1:12 | 15:1 to 2:1 | 5:1 |
| tetraconazole | 8:1 to 1:36 | 6:1 to 1:12 | 4:1 to 1:12 | 2:1 |
| thiabendazole | 45:1 to 1:4 | 15:1 to 1:2 | 11:1 to 2:1 | 4:1 |
| thifluzamide | 15:1 to 1:9 | 5:1 to 1:3 | 3:1 to 1:3 | 1:1 |
| thiophanate | 45:1 to 1:3 | 15:1 to 2:1 | 11:1 to 2:1 | 4:1 |
| thiophanate-methyl | 45:1 to 1:3 | 15:1 to 2:1 | 11:1 to 2:1 | 4:1 |
| thiram | 150:1 to 1:2 | 50:1 to 2:1 | 37:1 to 5:1 | 14:1 |
| tiadinil | 12:1 to 1:9 | 4:1 to 1:3 | 2:1 to 1:3 | 1:1 |
| tolclofos-methyl | 150:1 to 1:2 | 50:1 to 2:1 | 37:1 to 5:1 | 14:1 |
| tolprocarb | 20:1 to 1:20 | 5:1 to 1:5 | 3:1 to 1:3 | 1:1 |
| tolylfluanid | 150:1 to 1:36 | 50:1 to 1:12 | 15:1 to 2:1 | 5:1 |
| triadimefon | 15:1 to 1:36 | 5:1 to 1:12 | 3:1 to 1:5 | 2:1 |
| triadimenol | 15:1 to 1:36 | 5:1 to 1:12 | 3:1 to 1:5 | 2:1 |
| triarimol | 8:1 to 1:36 | 6:1 to 1:12 | 4:1 to 1:12 | 2:1 |
| triazoxide | 150:1 to 1:36 | 50:1 to 1:12 | 15:1 to 2:1 | 5:1 |
| tricyclazole | 15:1 to 1:9 | 5:1 to 1:3 | 3:1 to 1:3 | 1:1 |
| tridemorph | 30:1 to 1:3 | 10:1 to 1:1 | 7:1 to 1:1 | 3:1 |
| trifloxystrobin | 6:1 to 1:18 | 2:1 to 1:6 | 2:1 to 1:4 | 1:1 |
| triflumizole | 15:1 to 1:9 | 5:1 to 1:3 | 3:1 to 1:3 | 2:1 |
| triforine | 15:1 to 1:9 | 5:1 to 1:3 | 3:1 to 1:3 | 1:1 |
| trimorphamide | 45:1 to 1:9 | 15:1 to 1:3 | 7:1 to 1:2 | 2:1 |
| triticonazole | 15:1 to 1:36 | 5:1 to 1:12 | 3:1 to 1:5 | 2:1 |
| uniconazole | 15:1 to 1:36 | 5:1 to 1:12 | 3:1 to 1:5 | 2:1 |
| validamycin | 150:1 to 1:36 | 50:1 to 1:12 | 3:1 to 1:3 | 1:1 |
| valifenalate | 6:1 to 1:18 | 2:1 to 1:6 | 2:1 to 1:4 | 1:1 |
| vinclozolin | 120:1 to 1:2 | 40:1 to 2:1 | 15:1 to 2:1 | 6:1 |
| zineb | 150:1 to 1:2 | 50:1 to 2:1 | 37:1 to 5:1 | 14:1 |
| ziram | 150:1 to 1:2 | 50:1 to 2:1 | 37:1 to 5:1 | 14:1 |
| zoxamide | 6:1 to 1:18 | 2:1 to 1:6 | 2:1 to 1:4 | 1:1 |
| N-[[(cyclopropylmethoxy)amino][6-(difluoromethoxy)-2,3-difluorophenyl]-methylene]benzeneacetamide | 1:1 to 1:90 | 1:2 to 1:30 | 1:2 to 1:24 | 1:7 |
| N-[2-[4-[[3-(4-chlorophenyl)-2-propyn-1-yl]oxy]-3-methoxyphenyl]ethyl]-3-methyl-2-[(methylsulfonyl)amino]butanamide | 6:1 to 1:18 | 2:1 to 1:6 | 2:1 to 1:4 | 1:1 |
| N-[2-[4-[[3-(4-chlorophenyl)-2-propyn-1-yl]oxy]-3-methoxyphenyl]ethyl]-3-methyl-2-[(ethylsulfonyl)amino]butanamide | 6:1 to 1:18 | 2:1 to 1:6 | 2:1 to 1:4 | 1:1 |
| 3-[5-(4-chlorophenyl)-2,3-dimethyl-3-isoxazolidinyl]pyridine | 15:1 to 1:9 | 5:1 to 1:3 | 3:1 to 1:3 | 1:1 |

TABLE A1-continued

| Component (b) | Typical Weight Ratio | More Typical Weight Ratio | Most Typical Weight Ratio | Illustrative Weight Ratio |
|---|---|---|---|---|
| 4-fluorophenyl N-[1-[[[1-(4-cyanophenyl)-ethyl]sulfonyl]methyl]propyl]carbamate | 6:1 to 1:18 | 2:1 to 1:6 | 2:1 to 1:4 | 1:1 |
| 5-chloro-6-(2,4,6-trifluorophenyl)-7-(4-methylpiperidin-1-yl)[1,2,4]triazolo[1,5-a]pyrimidine | 15:1 to 1:36 | 5:1 to 1:12 | 1:1 to 1:6 | 1:2 |
| N-(4-chloro-2-nitrophenyl)-N-ethyl-4-methylbenzenesulfonamide | 15:1 to 1:18 | 5:1 to 1:6 | 3:1 to 1:3 | 1:1 |
| N'-[4-[4-chloro-3-(trifluoromethyl)phenoxy]-2,5-dimethylphenyl]-N-ethyl-N-methylmethanimidamide | 15:1 to 1:18 | 5:1 to 1:6 | 3:1 to 1:3 | 1:1 |
| N'-[4-[[3-[(4-chlorophenyl)methyl]-1,2,4-thiadiazol-5-yl]oxy]-2,5-dimethylphenyl]-N-ethyl-N-methylmethanimidamide | 20:1 to 1:20 | 8:1 to 1:8 | 3:1 to 1:3 | 1:1 |
| 1,1-dimethylethyl N-[6-[[[(Z)-[(1-methyl-1H-tetrazol-5-yl)phenylmethylene]amino]oxy]methyl]-2-pyridinyl]carbamate | 1:40 to 10:1 | 1:10 to 3:1 | 1:5 to 2:1 | 1:1 |
| 3-butyn-1-yl N-[6-[[[(Z)-[(1-methyl-1H-tetrazol-5-yl)phenylmethylene]amino]oxy]methyl]-2-pyridinyl]carbamate | 1:40 to 10:1 | 1:10 to 3:1 | 1:5 to 2:1 | 1:1 |
| pentyl N-[6-[[[[(1-methyl-1H-tetrazol-5-yl)-phenylmethylene]amino]oxy]methyl]-2-pyridinyl]carbamate | 1:9 to 18:1 | 1:3 to 6:1 | 1:3 to 3:1 | 1:1 |
| 2,6-dimethyl-1H,5H-[1,4]dithiino[2,3-c:5,6-c']dipyrrole-1,3,5,7(2H,6H)-tetrone | 1:1 to 400:1 | 4:1 to 100:1 | 8:1 to 50:1 | 10:1 |
| 2-[[[3-(2,6-dichlorophenyl)-1-methyl-2-propen-1-ylidene]amino]oxy]methyl]-α-(methoxyimino)-N-methylbenzeneacetamide (alternateively named (αE)-2-[[[(E)-[(2E)-3-(2,6-dichlorophenyl)-1-methyl-2-propen-1-ylidene]amino]oxy]methyl]-α-(methoxyimino)-N-methylbenzeneacetamide) (fenaminstrobin, Reg. No. 366815-39-6) | 1:9 to 18:1 | 1:3 to 6:1 | 1:3 to 3:1 | 1:1 |
| 5-fluoro-2-[(4-methylphenyl)methoxy]-4-pyrimidinamine | 1:20 to 20:1 | 1:5 to 5:1 | 1:3 to 3:1 | 1:1 |
| 5-fluoro-2-[(4-fluorophenyl)methoxy]-4-pyrimidinamine | 1:20 to 20:1 | 1:5 to 5:1 | 1:3 to 3:1 | 1:1 |
| 2-butoxy-6-iodo-3-propyl-4H-1-benzopyran-4-one | 3:1 to 1:36 | 1:1 to 1:12 | 1:1 to 1:12 | 1:3 |
| 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone (b46.1) (oxathiapiprolin, Reg. No. 1003318-67-9) | 1:400 to 1:1 | 1:100 to 1:1 | 1:50 to 1:2 | 1:3 |
| 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone (b46.1a) | 1:800 to 1:2 | 1:200 to 1:2 | 1:100 to 1:2 | 1:3 |
| (2-chloro-6-fluorophenyl)methyl 2-[1-[2-[3,5-bis(difluoromethyl)-1H-pyrazol-1-yl]acetyl]-4-piperidinyl]-4-thiazolecarboxylate (b46.2a) | 1:200 to 1:1 | 1:50 to 1:2 | 1:25 to 1:2 | 1:3 |
| (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate (b46.2b) | 1:200 to 1:1 | 1:50 to 1:2 | 1:25 to 1:2 | 1:3 |
| 1-[4-[4-[5-[(2,6-difluorophenoxy)methyl]-4,5-dihydro-3-isoxazolyl]-2-thiazolyl]-1-piperdinyl]-2-[5-methyl-3-(trifluoromethyl)-1H-pyrazol-1-yl]ethanone (b46.3a) | 1:200 to 1:1 | 1:50 to 1:2 | 1:25 to 1:2 | 1:3 |
| [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]-carbonyl]-3-pyridinyl]oxy]methyl 2-methylpropanoate (b46.4a) | 1:200 to 1:1 | 1:50 to 1:2 | 1:25 to 1:2 | 1:4 |
| (3S,6S,7R,8R)-3-[[[3-(acetyloxy)-4-methoxy-2-pyridinyl]carbonyl]amino]-6-methyl-4,9-dioxo-8-(phenylmethyl)-1,5-dioxonan-7-yl 2-methylpropanoate (b46.4b) | 1:200 to 1:1 | 1:50 to 1:2 | 1:25 to 1:2 | 1:4 |
| (3S,6S,7R,8R)-3-[[[3-[(acetyloxy)methoxy]-4-methoxy-2-pyridinyl]carbonyl]amino]-6-methyl-4,9-dioxo-8-(phenylmethyl)-1,5-dioxonan-7-yl 2-methylpropanoate (b46.4c) | 1:200 to 1:1 | 1:50 to 1:2 | 1:25 to 1:2 | 1:4 |

TABLE A1-continued

| Component (b) | Typical Weight Ratio | More Typical Weight Ratio | Most Typical Weight Ratio | Illustrative Weight Ratio |
|---|---|---|---|---|
| (3S,6S,7R,8R)-3-[[[4-methoxy-3-[[(2-methyl-propoxy)carbonyl]oxy]-2-pyridinyl]-carbonyl]amino]-6-methyl-4,9-dioxo-8-(phenylmethyl)-1,5-dioxonan-7-yl 2-methylpropanoate (b46.4d) | 1:200 to 1:1 | 1:50 to 1:2 | 1:25 to 1:2 | 1:4 |
| N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenylmethyl)-L-arabinonoyl]-L-serine, (1→4')-lactone (b46.4e) | 1:200 to 1:1 | 1:50 to 1:2 | 1:25 to 1:2 | 1:4 |
| 5,8-difluoro-N-[2-[3-methoxy-4-[[4-(trifluoromethyl)-2-pyridinyl]oxy]phenyl]-ethyl]-4-quinazolinamine (b46.5) | 1:40 to 10:1 | 10:1 to 3:1 | 1:5 to 2:1 | 1:1 |
| N-(3',4'-difluoro[1,1'-biphenyl]-2-yl)-3-(trifluoromethyl)-2-pyrazinecarboxamide (b46.6) | 1:20 to 20:1 | 5:1 to 1:5 | 1:3 to 3:1 | 1:1 |
| 3-(difluoromethyl)-N-[4-fluoro-2-(1,1,2,3,3,3-hexafluoropropoxy)phenyl]-1-methyl-1H-pyrazole-4-carboxamide (b46.7a) | 1:20 to 20:1 | 1:5 to 5:1 | 1:3 to 3:1 | 1:1 |
| 3-(difluoromethyl)-1-methyl-N-[2-(1,1,2,2-tetrafluoroethoxy)phenyl]-1H-pyrazole-4-carboxamide (b46.7b) | 1:20 to 20:1 | 1:5 to 5:1 | 1:3 to 3:1 | 1:1 |
| 2-[(3-bromo-6-quinolinyl)oxy]-N-(1,1-dimethyl-2-butyn-1-yl)-2-(methylthio)acetamide (b46.8a) | 1:5 to 22:1 | 1:2 to 8:1 | 1:2 to 4:1 | 1:1 |
| 2-[(3-ethynyl-6-quinolinyl)oxy]-N-[1-(hydroxymethyl)-1-methyl-2-propyn-1-yl]-2-(methylthio)acetamide (b46.8b) | 1:5 to 22:1 | 1:2 to 8:1 | 1:2 to 4:1 | 1:1 |
| N-(1,1-dimethyl-2-butyn-1-yl)-2-[(3-ethynyl-6-quinolinyl)oxy]-2-(methylthio)acetamide (b46.8c) | 1:5 to 22:1 | 1:2 to 8:1 | 1:2 to 4:1 | 1:1 |
| 2-[(3-bromo-8-methyl-6-quinolinyl)oxy]-N-(1,1-dimethyl-2-propyn-1-yl)-2-(methylthio)acetamide (b46.8d) | 1:5 to 22:1 | 1:2 to 8:1 | 1:2 to 4:1 | 1:1 |
| 2-[(3-bromo-6-quinolinyl)oxy]-N-(1,1-dimethylethyl)butanamide (b46.8e) | 1:5 to 22:1 | 1:2 to 8:1 | 1:2 to 4:1 | 1:1 |
| N-[2-(2,4-dichlorophenyl)-2-methoxy-1-methylethyl]-3-(difluoromethyl)-1-methyl-1H-pyrazole-4-carboxamide | 1:20 to 20:1 | 1:5 to 5:1 | 1:3 to 3:1 | 1:1 |
| α-[methoxyimino]-N-methyl-2-[[[1-[3-(trifluoromethyl)phenyl]ethoxy]imino]-methyl]benzeneacetamide | 1:9 to 18:1 | 1:3 to 6:1 | 1:3 to 3:1 | 1:2 |
| N-cyclopropyl-3-(difluoromethyl)-5-fluoro-1-methyl-N-[[2-(1-methylethyl)phenyl]methyl]-1H-pyrazole-4-carboxamide | 1:9 to 18:1 | 1:3 to 6:1 | 1:3 to 3:1 | 1:1 |
| 1-[[(2S,3R)-3-(2-chlorophenyl)-2-(2,4-difluorophenyl)-2-oxiranyl]methyl]-1H-1,2,4-triazole (b46.9a) | 8:1 to 1:36 | 6:1 to 1:12 | 4:1 to 1:12 | 2:1 |
| 2-[[(2S,3R)-3-(2-chlorophenyl)-2-(2,4-difluorophenyl)-2-oxiranyl]methyl]-1,2-dihydro-3H-1,2,4-triazole-3-thione (b46.9b) | 8:1 to 1:36 | 6:1 to 1:12 | 4:1 to 1:12 | 2:1 |
| 1-[[(2S,3R)-3-(2-chlorophenyl)-2-(2,4-difluorophenyl)-2-oxiranyl]methyl]-5-(2-propen-1-ylthio)-1H-1,2,4-triazole (b46.9c) | 8:1 to 1:36 | 6:1 to 1:12 | 4:1 to 1:12 | 2:1 |
| α-[3-(4-chloro-2-fluorophenyl)-5-(2,4-difluorophenyl)-4-isoxazolyl]-3-pyridinemethanol (b46.10a) | 8:1 to 1:36 | 6:1 to 1:12 | 4:1 to 1:12 | 2:1 |
| (αS)-[3-(4-chloro-2-fluorophenyl)-5-(2,4-difluorophenyl)-4-isoxazolyl]-3-pyridinemethanol (b46.10b) | 8:1 to 1:36 | 6:1 to 1:12 | 4:1 to 1:12 | 2:1 |
| (αR)-[3-(4-chloro-2-fluorophenyl)-5-(2,4-difluorophenyl)-4-isoxazolyl]-3-pyridinemethanol (b46.10c) | 8:1 to 1:36 | 6:1 to 1:12 | 4:1 to 1:12 | 2:1 |
| 3-[2-[3-(4-chloro-2-fluorophenyl)-5-(2,4-difluorophenyl)-4-isoxazolyl]-2-oxiranyl]pyridine (b46.10d) | 8:1 to 1:36 | 6:1 to 1:12 | 4:1 to 1:12 | 2:1 |
| α-(1-chlorocyclopropyl)-α-[2-(2,2-dichlorocyclopropyl)ethyl]-1H-1,2,4-triazole-1-ethanol | 8:1 to 1:36 | 6:1 to 1:12 | 4:1 to 1:12 | 2:1 |
| 2-[2-(1-chlorocyclopropyl)-4-(2,2-dichlorocyclopropyl)-2-hydroxybutyl]-1,2-dihydro-3H-1,2,4-triazole-3-thione | 8:1 to 1:36 | 6:1 to 1:12 | 4:1 to 1:12 | 2:1 |
| 2-[(2,5-dimethylphenoxy)methyl]-α-methoxy-N-benzeneacetamide (mandestrobin, Reg. No. 173662-97-0) | 9:1 to 1:18 | 3:1 to 1:6 | 2:1 to 1:4 | 1:1 |

TABLE A1-continued

| Component (b) | Typical Weight Ratio | More Typical Weight Ratio | Most Typical Weight Ratio | Illustrative Weight Ratio |
|---|---|---|---|---|
| methyl (α-E)-2-[[(3-butyl-4-methyl-2-oxo-2H-1-benzopyran-7-yl)oxy]methyl]-α-(methoxymethylene)benzeneacetate (coumoxystrobin, Reg. No. 850881-70-8) | 9:1 to 1:18 | 3:1 to 1:6 | 2:1 to 1:4 | 1:1 |
| methyl (αE)-2-[[[(E)-[(2E)-3-(4-chlorophenyl)-1-methyl-2-propen-1-ylidene]amino]oxy]methyl]-α-(methoxymethylene)benzeneacetate (enoxystrobin, Reg. No. 238410-11-2) | 9:1 to 1:18 | 3:1 to 1:6 | 2:1 to 1:4 | 1:1 |
| methyl (αE)-2-[[2-chloro-4-(trifluoromethyl)phenoxy]methyl]-α-(methoxymethylene)benzeneacetamide (flufenoxystrobin, Reg. No. 918162-02-4) | 9:1 to 1:18 | 3:1 to 1:6 | 2:1 to 1:4 | 1:1 |
| methyl N-methoxy-N-[2-[[(3,5,6-trichloro-2-pyridinyl)oxy]methyl]phenyl]carbamate (triclopyricarb, Reg. No. 902760-40-1) | 9:1 to 1:18 | 3:1 to 1:6 | 2:1 to 1:4 | 1:1 |
| flometoquin | 9:1 to 1:18 | 3:1 to 1:6 | 2:1 to 1:4 | 1:1 |

| Table Number | Component (a) Column Entry |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |

Formulation/Utility

A compound of Formula 1 of this invention (including N-oxides and salts thereof) will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1 and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects*, 1994 BCPC Monograph No. 57, and references listed therein.

For further information regarding the art of formulation, see T. S. Woods, "The Formulator's Toolbox-Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

EXAMPLE A

| High Strength Concentrate | |
|---|---|
| Any one of Compounds 1, 2, 3, 4, 5, 6, 7, 8, 9, 10, 11, 12, 13, 14, 15 and 16 | 98.5% |
| silica aerogel | 0.5% |
| synthetic amorphous fine silica | 1.0% |

EXAMPLE B

| Wettable Powder | |
|---|---|
| Any one of Compounds 1, 2, 3, 4, 5, 6, 7, 8, 9, 10, 11, 12, 13, 14, 15 and 16 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

| Granule | |
|---|---|
| Any one of Compounds 1, 2, 3, 4, 5, 6, 7, 8, 9, 10, 11, 12, 13, 14, 15 and 16 | 10.0% |
| attapulgite granules (low volatile matter, 0.71/0.30 mm; U.S.S. No. 25-50 sieves) | 90.0% |

EXAMPLE D

| Extruded Pellet | |
|---|---|
| Any one of Compounds 1, 2, 3, 4, 5, 6, 7, 8, 9, 10, 11, 12, 13, 14, 15 and 16 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

| Emulsifiable Concentrate | |
|---|---|
| Any one of Compounds 1, 2, 3, 4, 5, 6, 7, 8, 9, 10, 11, 12, 13, 14, 15 and 16 | 10.0% |
| polyoxyethylene sorbitol hexoleate | 20.0% |
| $C_6$-$C_{10}$ fatty acid methyl ester | 70.0% |

EXAMPLE F

| Microemulsion | |
|---|---|
| Any one of Compounds 1, 2, 3, 4, 5, 6, 7, 8, 9, 10, 11, 12, 13 14, 15 and 16 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

| Seed Treatment | |
|---|---|
| Any one of Compounds 1, 2, 3, 4, 5, 6, 7, 8, 9, 10, 11, 12, 13, 14, 15 and 16 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Water-soluble and water-dispersible formulations are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

Seed is normally treated at a rate of from about 0.001 g (more typically about 0.1 g) to about 10 g per kilogram of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligenea*, *Podosphaera leucotricha* and *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici* repentis and *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite*, *Puccinia striiformis*, *Puccinia hordei*, *Puccinia graminis* and *Puccinia arachidis*), *Hemileia vastatrix* and *Phakopsora pachyrhizi*; other pathogens including *Rutstroemia floccosum* (also known as Sclerotina homoeocarpa); *Rhizoctonia* spp. (such as *Rhizoctonia solani*); *Fusarium* diseases such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; *Rhizopus* spp. (such as *Rhizopus stolonifer*); *Aspergillus* spp. (such as *Aspergillus flavus* and *Aspergillus parasiticus*); and other genera and species closely related to these pathogens. In addition to their fungicidal activity, the compositions or combinations also have activity against bacteria such as *Erwinia amylovora*, *Xanthomonas campestris*, *Pseudomonas syringae*, and other related species. By controlling harmful microorganisms, the compounds of the invention are useful for improving (i.e. increasing) the ratio of beneficial to harmful microorganisms in contact with crop plants or their propagules (e.g., seeds, corms, bulbs, tubers, cuttings) or in the agronomic environment of the crop plants or their propagules.

Compounds of this invention are useful in seed treatments for protecting seeds from plant diseases. In the context of the present disclosure and claims, treating a seed means contacting the seed with a biologically effective amount of a compound of this invention, which is typically formulated as a composition of the invention. This seed treatment protects the seed from soil-borne disease pathogens and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with compounds of this invention can also increase vigor of plants growing from the seed.

Compounds of this invention and their compositions, both alone and in combination with other fungicides, nematicides and insecticides, are particularly useful in seed treatment for crops including, but not limited to, maize or corn, soybeans, cotton, cereal (e.g., wheat, oats, barley, rye and rice), potatoes, vegetables and oilseed rape.

Furthermore, the compounds of this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g, fruits, seeds, foliage, stems, bulbs. tubers) can be stored refrigerated or un-refrigerated after harvest, and remain edible and free from noticeable or harmful degradation or contamination by fungi or other microorganisms. Treatment of edible plant parts before or after harvest with compounds of the invention can also decrease the formation of toxic metabolites of fungi or other microorganisms, for example mycotoxins such as aflatoxins.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants. Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.001 g (more typically about 0.1) to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

Of note is a composition which in addition to the compound of Formula 1 include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-)pyrimidine fungicides; (9) anilinopyrimidine fungicides; (10) N-phenyl carbamate fungicides; (11) quinone outside inhibitor (QoI) fungicides; (12) phenylpyrrole fungicides; (13) quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

One skilled in the art will understand classes (1) through (46) refer to either component (b1) through (b46) or (c1) through (c46) as described in the Summary of the Invention or any of the Embodiments described herein. Further descriptions of classes (1) through (46) of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure.

Methyl benzimidazole carbamate fungicides include benzimidazoles and thiophanates. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. Demethylation fungicides include azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole, 1-[[(2S,3R)-3-(2-chlorophenyl)-2-(2,4-difluorophenyl)-2-oxiranyl]methyl]-1H-1,2,4-triazole, 2-[[(2S,3R)-3-(2-chlorophenyl)-2-(2,4-difluorophenyl)-2-oxiranyl]methyl]-1,2-dihydro-3H-1,2,4-triazole-3-thione, 1-[[(2S,3R)-3-(2-chlorophenyl)-2-(2,4-difluoro-phenyl)-2-oxiranyl]methyl]-5-(2-propen-1-ylthio)-1H-1,2,4-triazole, α-(1-chloro-cyclopropyl)-α-[2-(2,2-dichlorocyclopropyl)ethyl]-1H-1,2,4-triazole-1-ethanol and 2-[2-(1-chlorocyclopropyl)-4-(2,2-dichlorocyclopropyl)-2-hydroxybutyl]-1,2-dihydro-3H-1,2,4-triazole-3-thione. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanines, oxazolidinones and butyrolactones. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholines, piperidines and spiroketal-amines. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phophorothiolates and dithiolanes. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides, pyridine carboxamides and thiophene carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, isopyrazam, benzovindiflupyr, N-[2-(1S, 2R)-[1,1'-bicyclopropyl]-2-ylphenyl]-3-(difluoromethyl)-1-methyl-1H-pyrazole-4-carboxamide penflufen, (N-[2-(1,3-dimethylbutyl)phenyl]-5-fluoro-1,3-dimethyl-1H-pyrazole-4-carboxamide), N-[2-(2,4-dichlorophenyl)-2-methoxy-1-methylethyl]3-(difluoromethyl)-1-methyl-1H-pyrazole-4-carboxamide and N-cyclopropyl-3-(difluoromethyl)-5-fluoro-1-methyl-N-[[2-(1-methylethyl)phenyl]methyl]-1H-pyrazole-4-carboxamide. The pyridine carboxamides include boscalid. The thiophene carboxamides include isofetamid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylates, methoxycarbamates, oximinoacetates, oximinoacetamides, oxazolidinediones, dihydrodioxazines, imidazolinones and benzylcarbamates. The methoxyacrylates include azoxystrobin, enestroburin (SYP-Z071), picoxystrobin and pyraoxystrobin (SYP-3343). The methoxycarbamates include pyraclostrobin and pyrametostrobin (SYP-4155). The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide. The oxazolidinediones include famoxadone. The dihydrodioxazines include fluoxastrobin. The imidazolinones include fenamidone. The benzylcarbamates include pyribencarb. Class (11) also includes 2-[(2,5-dimethylphenoxy)methyl]-α-methoxy-N-benzeneacetamide (mandestrobin Reg. No. 173662-97-0), methyl (α-E)-2-[[(3-butyl-4-methyl-2-oxo-2H-1-benzopyran-7-yl)oxy]methyl]-α-(methoxymethylene)benzeneacetate (coumoxystrobin, Reg. No. 850881-70-8), methyl (αE)-2-[[[(E)-[(2E)-3-(4-chlorophenyl)-1-methyl-2-propen-1-ylidene]amino]oxy]methyl]-α-(methoxymethylene)benzeneacetate (enoxystrobin, Reg. No. 238410-11-2), methyl (αE)-2-[[2-chloro-4-(trifluoromethyl)phenoxy]methyl]-α-(methoxymethylene)benzeneacetamide (flufenoxystrobin, Reg. No. 918162-02-4) and methyl N-methoxy-N-[2-[[(3,5,6-trichloro-2-pyridinyl)oxy]methyl]phenyl]carbamate (triclopyricarb, Reg. No. 902760-40-1).

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen and tebufloquin are examples of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbons and 1,2,4-thiadiazoles. The aromatic carbon fungicides include biphenyl, chloroneb, dicloran, quintozene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranones, pyrroloquinolinones and triazolobenzothiazoles. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamides, carboxamides and propionamides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamates and allylaminess. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi Inhibiting mitochondrial respiration prevents normal fungal growth and development. Quinone inside inhibitor fungicides include cyanoimidazoles and sulfamoyltriazoles. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly. Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazoles and isothiazolones. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amides, valinamide carbamates, carbamates and mandelic acid amides. The cinnamic acid amides include dimethomorph and flumorph. The valinamide carbamates include benthiavalicarb, benthiavalicarb-isopropyl, iprovalicarb, valifenalate and valiphenal. The carbamates include tolprocarb. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)-amino]butanamide and N-[2-[4-[[3-(4-chlorophenyl)-2-propyn-1-yl]oxy]-3-methoxyphenyl]-ethyl]-3-methyl-2-[(ethylsulfonyl)amino] butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. Host plant defense induction fungicides include benzo-thiadiazoles, benzisothiazoles and thiadiazole-carboxamides. The benzo-thiadiazoles include acibenzolar-S-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: "thiazole carboxamide fungicides" (Fungicide Resistance Action Committee (FRAC) code U5), "phenyl-acetamide fungicides" (Fungicide Resistance Action Committee (FRAC) code U6), "quinazolinone fungicides" (Fungicide Resistance Action Committee (FRAC) code U7), "benzophenone fungicides" (Fungicide Resistance Action Committee (FRAC) code U8) and "triazolopyrimidine fungicides". The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid. The benzophenones include metrafenone. The triazolopyrimidines include ametoctradin. Class (46) (i.e. "Fungicides other than classes (1) through (45)") also includes bethoxazin, fluxapyroxad, flometoquin, neo-asozin (ferric methanearsonate), pyriofenone, pyrrolnitrin, quinomethionate, tebufloquin, N-[2-[4-[[3-(4-chlorophenyl)-2-propyn-1-yl]oxy]-3-methoxyphenyl]ethyl]-3-methyl-2-[(methylsulfonyl)amino] butanamide, N-[2-[4-[[3-(4-chlorophenyl)-2-propyn-1-yl] oxy]-3-methoxyphenyl]ethyl]-3-methyl-2-[(ethylsulfonyl) amino]butanamide, flutianil (2-[[2-fluoro-5-

(trifluoromethyl)phenyl]thio]-2-[3-(2-methoxyphenyl)-2-thiazolidinylidene]acetonitrile), 3-[5-(4-chlorophenyl)-2,3-dimethyl-3-isoxazolidinyl]pyridine (alternatively named 3-[(3R)-5-(4-chlorophenyl)-2,3-dimethyl-3-isoxazolidinyl]pyridine) (pyrisoxazole), 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl)[1,2,4]triazolo[1,5-a]pyrimidine (BAS600), N-(4-chloro-2-nitro-phenyl)-N-ethyl-4-methylbenzenesulfonamide, N-[4-[4-chloro-3-(trifluoromethyl)phenoxy]-2,5-dimethyl-phenyl]-N-ethyl-N-methylmethanimidamide, flupyrazamine (1-[(2-propenylthio)carbonyl]-2-(1-methylethyl)-4-(2-methylphenyl)-5-amino-1H-pyrazol-3-one), N-[4-[[3-[(4-chlorophenyl)methyl]-1,2,4-thiadiazol-5-yl]oxy]-2,5-dimethylphenyl]-N-ethyl-N-methyl-methanimidamide, 1,1-dimethylethyl N-[6-[[[[1-methyl-1H-tetrazol-5-yl)phenylmethylene]amino]oxy]methyl-2-pyridinyl]carbamate, 3-butyn-1-yl N-[6-[[[[1-methyl-1H-tetrazol-5-yl)phenylmethylene]amino]oxy]methyl]-2-pyridinyl]carbamate, 2,6-dimethyl-1H,5H-[1,4]dithiino[2,3-c:5,6-c']dipyrrole-1,3,5,7(2H,6H)-tetrone, 5-fluoro-2-[(4-methylphenyl)methoxy]-4-pyrimidinamine and 5-fluoro-2-[(4-fluorophenyl)methoxy]-4-pyrimidinamine.

"Fungicides other than fungicides of classes (1) through (45)" include certain fungicides whose mode of action may be unknown, or may not yet be classified. In a composition comprising (a) at least one compound selected from Formula 1, N-oxides, and salts thereof, with (b) at least one fungicidal compound selected from component (b), component (b46) is selected from components (b46.1) through (b46.9), as shown below.

Component (b46.1) relates to the compound of Formula b46.1

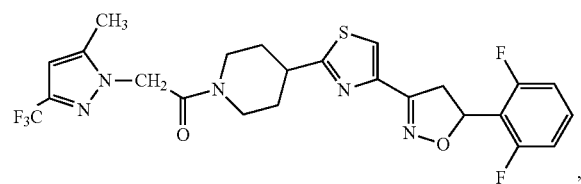

which is 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (oxathiapiprolin) Registry Number 1003318-67-9). Of note is (b46.1a) the R enantiomer of Formula b46.1

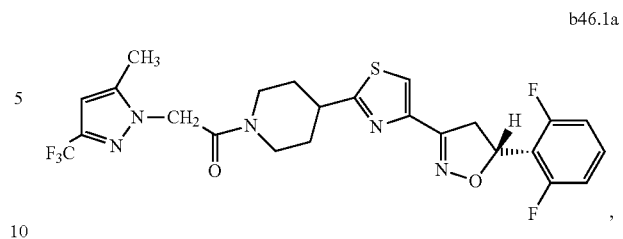

which is 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone (Registry Number 1003319-79-6). Methods for preparing the compound of Formula 46.1 are described in PCT Patent Publication WO 2008/013622.

Component (b46.2) relates to a compound of Formula b46.2

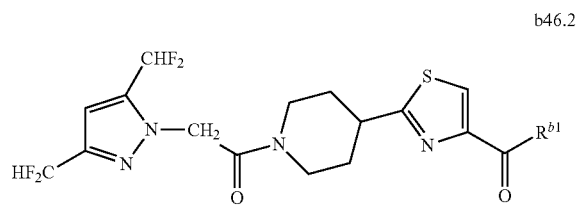

wherein $R^{b1}$ is

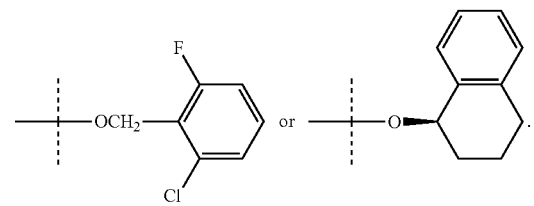

Examples of a compound of Formula b46.2 include (b46.2a) (2-chloro-6-fluorophenyl)-methyl 2-[1-[2-[3,5-bis(difluoromethyl)-1H-pyrazol-1-yl]acetyl]-4-piperidinyl]-4-thiazole-carboxylate (Registry Number 1299409-40-7) and (b46.2b) (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate (Registry Number 1299409-42-9). Methods for preparing compounds of Formula b46.2 are described in PCT Patent Publications WO 2009/132785 and WO 2011/051243.

Component (b46.3) relates to a compound of Formula b46.3

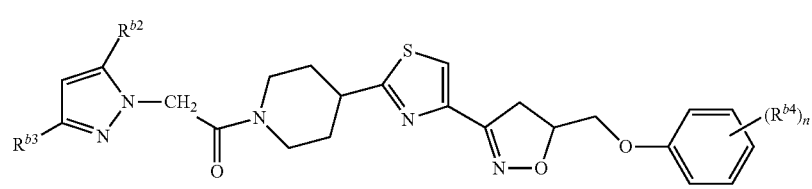

wherein $R^{b2}$ is $CH_3$, $CF_3$ or $CHF_2$; $R^{b3}$ is $CH_3$, $CF_3$ or $CHF_2$; $R^{b4}$ is halogen or cyano; and n is 0, 1, 2 or 3.

Examples of a compound of Formula b46.3 include (b46.3a) 1-[4-[4-[5-[(2,6-difluorophenoxy)methyl]-4,5-dihydro-3-isoxazolyl]-2-thiazolyl]-1-piperdinyl]-2-[5-methyl-3-(trifluoromethyl)-1H-pyrazol-1-yl]ethanone. Methods for preparing compounds of Formula b46.3 are described in PCT Patent Application PCT/US11/64324.

Component (b46.4) relates to a compound of Formula b46.4

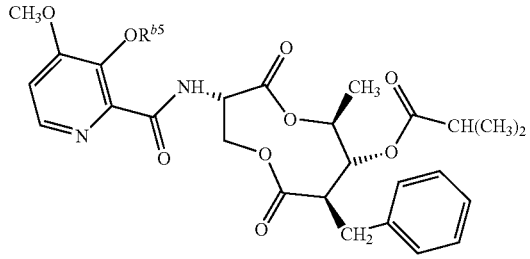

wherein $R^{b5}$ is —$CH_2OC(O)CH(CH_3)_2$, —$C(O)CH_3$, —$CH_2OC(O)CH_3$, —$C(O)OCH_2CH(CH_3)_2$ or

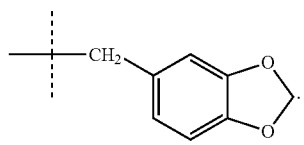

Examples of a compound of Formula b46.4 include (b46.4a) [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropanoate (Registry Number 517875-34-2), (b46.4b) (3S,6S,7R,8R)-3-[[[3-(acetyloxy)-4-methoxy-2-pyridinyl]-carbonyl]amino]-6-methyl-4,9-dioxo-8-(phenylmethyl)-1,5-dioxonan-7-yl 2-methyl-propanoate (Registry Number 234112-93-7), (b46.4c) (3S,6S,7R,8R)-3-[[[3-[(acetyloxy)methoxy]-4-methoxy-2-pyridinyl]carbonyl]amino]-6-methyl-4,9-dioxo-8-(phenylmethyl)-1,5-dioxonan-7-yl 2-methylpropanoate (Registry Number 517875-31-9), (b46.4d) (3S,6S,7R,8R)-3-[[[4-methoxy-3-[[(2-methylpropoxy)carbonyl]oxy]-2-pyridinyl]-carbonyl]amino]-6-methyl-4,9-dioxo-8-(phenylmethyl)-1,5-dioxonan-7-yl 2-methylpropanoate (Registry Number 328256-72-0), and (b46.4e) N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenylmethyl)-L-arabinonoyl]L-serine, (1→4')-lactone (Registry Number 1285706-70-8). Methods for preparing compounds of Formula b46.4 are described in PCT Patent Publications WO 99/40081, WO 2001/014339, WO 2003/035617 and WO 2011044213.

Component (b46.5) relates to the compound of Formula 46.5

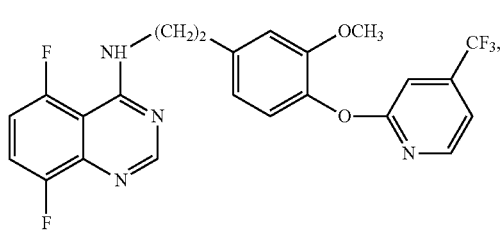

which is 5,8-difluoro-N-[2-[3-methoxy-4-[[4-(trifluoromethyl)-2-pyridinyl]oxy]phenyl]-ethyl]-4-quinazolinamine (Registry Number 1210070-31-7). The compound of Formula b46.5 can be prepared by methods described in PCT Patent Publication WO 2010/025451.

Component (b46.6) relates to the compound of Formula b46.6

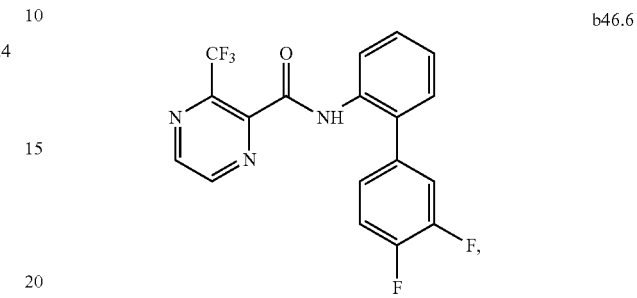

which is N-(3',4'-difluoro[1,1'-biphenyl]-2-yl)-3-(trifluoromethyl)-2-pyrazinecarboxamide (Registry Number 942515-63-1). The compound of Formula b46.6 can be prepared by methods described in PCT Patent Publication WO 2007/072999.

Component (b46.7) relates to a compound of Formula b46.7

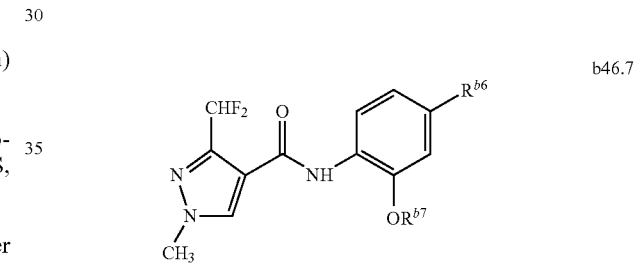

wherein $R^{b6}$ is H or F, and $R^{b7}$ is —$CF_2CHFCF_3$ or —$CF_2CF_2H$. Examples of a compound of Formula b46.7 are (b46.7a) 3-(difluoromethyl)-N-[4-fluoro-2-(1,1,2,3,3,3-hexafluoro-propoxy)phenyl]-1-methyl-1H-pyrazole-4-carboxamide (Registry Number 1172611-40-3) and (b46.7b) 3-(difluoromethyl)-1-methyl-N-[2-(1,1,2,2-tetrafluoroethoxy)phenyl]-1H-pyrazole-4-carboxamide (Registry Number 923953-98-4). Compounds of Formula 46.7 can be prepared by methods described in PCT Patent Publication WO 2007/017450.

Component b46.8 relates a compound of Formula b46.8

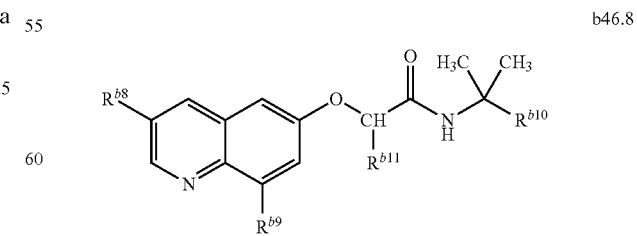

wherein
$R^{b8}$ is halogen, $C_1$-$C_4$ alkoxy or $C_2$-$C_4$ alkynyl;
$R^{b9}$ is H, halogen or $C_1$-$C_4$ alkyl;

Rb$^{10}$ is C$_1$-C$_{12}$ alkyl, C$_1$-C$_{12}$ haloalkyl, C$_1$-C$_{12}$ alkoxy, C$_2$-C$_{12}$ alkoxyalkyl, C$_2$-C$_{12}$ alkenyl, C$_2$-C$_{12}$ alkynyl, C$_4$-C$_{12}$ alkoxyalkenyl, C$_4$-C$_{12}$ alkoxyalkynyl, C$_1$-C$_{12}$ alkylthio or C$_2$-C$_{12}$ alkylthioalkyl;

R$^{b11}$ is methyl or —Y$^{b13}$—R$^{b12}$;

R$^{b12}$ is C$_1$-C$_2$ alkyl; and

Y$^{b13}$ is CH$_2$, O or S.

Examples of compounds of Formula b46.8 include (b46.8a) 2-[(3-bromo-6-quinolinyl)oxy]-N-(1,1-dimethyl-2-butyn-1-yl)-2-(methylthio)acetamide, (b46.8b) 2-[(3-ethynyl-6-quinolinyl)oxy]-N-[1-(hydroxymethyl)-1-methyl-2-propyn-1-yl]-2-(methylthio)acetamide, (b46.8c) N-(1,1-dimethyl-2-butyn-1-yl)-2-[(3-ethynyl-6-quinolinyl)oxy]-2-(methylthio)-acetamide, (b46.8d) 2-[(3-bromo-8-methyl-6-quinolinyl)oxy]-N-(1,1-dimethyl-2-propyn-1-yl)-2-(methylthio)acetamide and (b46.8e) 2-[(3-bromo-6-quinolinyl)oxy]-N-(1,1-dimethylethyl)butanamide.

Compounds of Formula b46.8, their use as fungicides and methods of preparation are generally known; see, for example, PCT Patent Publications WO 2004/047538, WO 2004/108663, WO 2006/058699, WO 2006/058700, WO 2008/110355, WO 2009/030469, WO 2009/049716 and WO 2009/087098.

Component (b46.9) relates to the compound of Formula b46.9

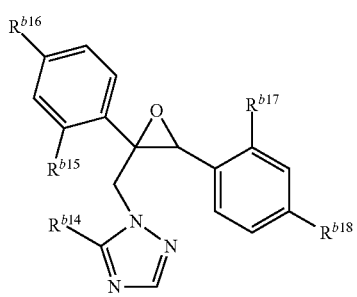

b46.9 wherein R$^{b14}$ is H, —SH, C$_1$-C$_6$ alkylthio, C$_1$-C$_6$ alkenylthio, C$_1$-C$_6$ alkynylthio or C$_4$-C$_7$ cycloalkylalkylthio; and R$^{b15}$, R$^{b16}$, R$^{b17}$ and R$^{b18}$ are each independently H or halogen; provided that at least one of R$^{b15}$, R$^{b16}$, R$^{b17}$ and R$^{b18}$ is other than H. Of note is a compound of Formula b46.9 wherein R$^{b14}$ and R$^{b18}$ are H; R$^{b15}$ and R$^{b16}$ are F; and R$^{b17}$ is Cl, shown below as the compound of Formula b46.9a

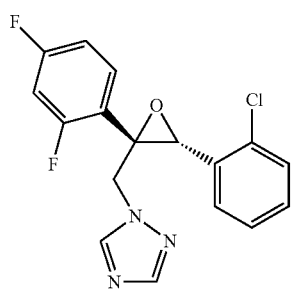

b46.9a which is 1-[[(2S,3R)-3-(2-chlorophenyl)-2-(2,4-difluorophenyl)-2-oxiranyl]methyl]-1H-1,2,4-triazole (Registry Number 1000181-79-2). Of note is a compound of Formula b46.9 wherein R$^{b14}$ is SH; R$^{b18}$ is H; R$^{b15}$ and R$^{b16}$ are F; and R$^{b17}$ is Cl, shown below as the compound of Formula b46.9b

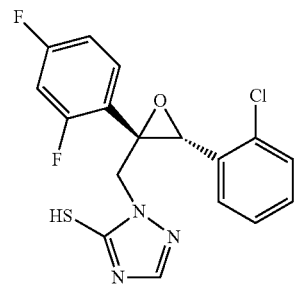

b46.9b which is 2-[[(2S,3R)-3-(2-chlorophenyl)-2-(2,4-difluorophenyl)-2-oxiranyl]methyl]-1,2-dihydro-3H-1,2,4-triazole-3-thione (Registry Number 1161442-71-2). Of note is a compound of Formula b46.9 wherein R$^{b14}$ is —SCH$_2$CH=CH$_2$; R$^{b18}$ is H; R$^{b15}$ and R$^{b16}$ are F; and R$^{b17}$ is Cl, shown below as the compound of Formula (b46.9c)

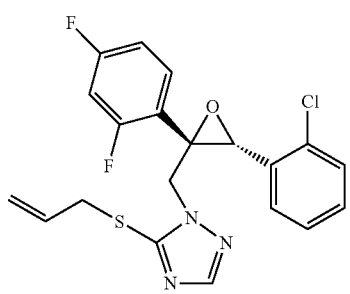

b46.9c which is 1-[[(2S,3R)-3-(2-chlorophenyl)-2-(2,4-difluorophenyl)-2-oxiranyl]methyl]-5-(2-propen-1-ylthio)-1H-1,2,4-triazole (Registry Number 1310803-80-5). Methods for preparing compounds of Formula b46.9 are described in PCT Patent Publications WO 2007/147778, WO 2011/069912 and WO 2009/077443.

Component (b46.10) relates to a compound of Formula b46.10

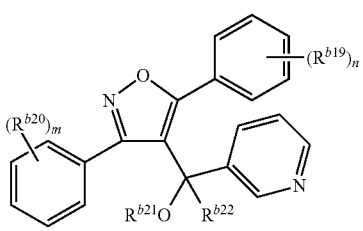

b46.10 wherein R$^{b19}$ and R$^{b20}$ are each independently halogen; R$^{b21}$ is H, CH$_3$, CHO or C(O)CH$_3$; R$^{b22}$ is H; or R$^{b21}$ and R$^{b22}$ are taken together as CH$_2$; and n and m are each independently 1 or 2. Of note is a compound of Formula b46.10 wherein (R$^{b19}$)$_n$ is 2,4-di-F; (R$^{b20}$)$_m$ is 2-F, 4-Cl; and R$^{b21}$ and R$^{b22}$ are each H, shown below as the compound of Formula b46.10a

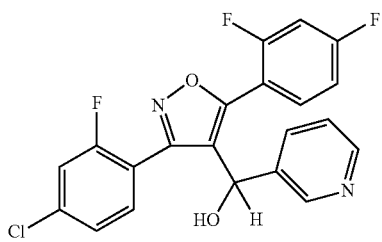

b46.10a which is α-[3-(4-chloro-2-fluorophenyl)-5-(2,4-difluorophenyl)-4-isoxazolyl]-3-pyridinemethanol (Registry Number 1229605-96-2). Of note is a compound of Formula b46.10 wherein $(R^{b19})_n$ is 2,4-di-F; $(R^{b20})_m$ is 2-F, 4-Cl; and $R^{b21}$ and $R^{b22}$ are each H (i.e. the S enantiomer), shown below as the compound of Formula b46.10b

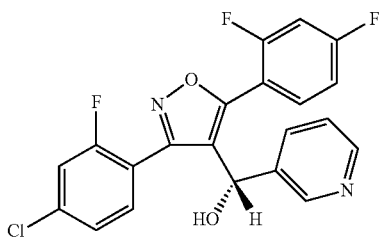

b46.10b which is (αS)-[3-(4-chloro-2-fluorophenyl)-5-(2,4-difluorophenyl)-4-isoxazolyl]-3-pyridinemethanol (Registry Number 1229606-46-5). Of note is a compound of Formula b46.10 wherein $(R^{b19})_n$ is 2,4-di-F; $(R^{b20})_m$ is 2-F; 4-Cl; and $R^{b21}$ and $R^{b22}$ are each H (i.e. the R enantiomer), shown below as the compound of Formula b46.10c

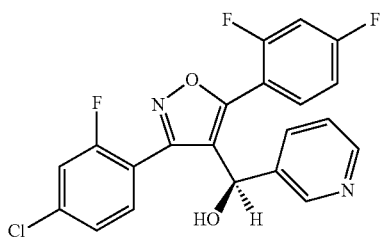

b46.10c which is (αR)-[3-(4-chloro-2-fluorophenyl)-5-(2,4-difluorophenyl)-4-isoxazolyl]-3-pyridinemethanol (Registry Number 1229606-02-3). Of note is a compound of Formula b46.10 wherein $(R^{b19})_n$ is 2,4-di-F; $(R^{b20})_m$ is 2-F, 4-Cl; and $R^{b21}$ and $R^{b22}$ are taken together as $CH_2$, shown below as the compound of Formula b46.10d

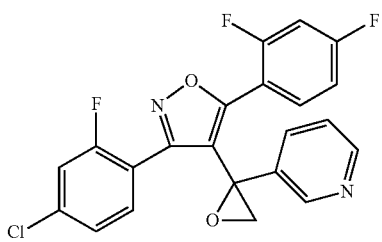

b46.10d which is 3-[2-[3-(4-chloro-2-fluorophenyl)-5-(2,4-difluorophenyl)-4-isoxazolyl]-2-oxiranyl]pyridine (Registry Number 1355373-06-6). Methods for preparing compounds of Formula b46.10 are described in PCT Patent Publications WO 2010/069882 and WO 2012/010568.

Therefore of note is a mixture (i.e. composition) comprising a compound of Formula 1 and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon, 2-hydroxy-4-oxo-1-(5-pyrimidinylmethyl)-3-[3-(trifluoromethyl)phenyl]-4H-pyrido[1,2-a]pyrimidinium inner salt and triflumuron; and biological agents including entomopathogenic bacteria, such as *Bacillus thuringiensis* subsp. *aizawai, Bacillus thuringiensis* subsp. kurstaki, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate) fungicides; (2) cymoxanil; (3) phenylamide fungicides; (4) proquinazid (6-iodo-3-propyl-2-propyloxy-4 (3H)-quinazolinone); (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin, pyrametostrobin, pyraoxystrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of further note are combinations of compounds of Formula 1 with azoxystrobin, kresoxim-methyl, trifloxystrobin, pyraclostrobin, pyraoxystrobin, pyrametostrobin, picoxystrobin, dimoxystrobin, metominostrobin/fenominostrobin, carbendazim, chlorothalonil, quinoxyfen, metrafenone, pyriofenone, cyflufenamid, fenpropidine, fenpropimorph, bromuconazole, cyproconazole, difenoconazole, epoxiconazole, fenbuconazole, flusilazole, hexaconazole, ipconazole, metconazole, myclobutanil, penconazole, propiconazole, proquinazid, prothioconazole, tebuconazole, triticonazole, famoxadone, prochloraz, penthiopyrad and boscalid (nicobifen). Fungicides of note for formulation with compounds of Formula 1 to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Insecticides or nematicides with which compounds of Formula 1 can be formulated to provide mixtures useful in seed treatment include but are not limited to abamectin, acetamiprid, acrinathrin, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

Compositions comprising compounds of Formula 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM I-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by *rhizobia* bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The following Tests demonstrate the control efficacy of compounds of this invention on specific pathogens. The pathogen control protection afforded by the compounds is not limited, however, to these species. See Index Table A for compound descriptions. The abbreviation "Ex." stands for "Example" and is followed by a number indicating in which example the compound is prepared. $^1$H NMR spectra are reported in ppm downfield from tetramethylsilane; "s" means singlet, "d" means doublet, "t" means triplet, "q" means quartet, "m" means multiplet, "br s" means broad singlet. Mass spectra (M.S.) are reported as the molecular weight of the highest isotopic abundance parent ion (M+1) formed by addition of H$^+$ (molecular weight of 1) to the molecule, observed by mass spectrometry using atmospheric pressure chemical ionization (AP$^+$). The presence of molecular ions containing one or more higher atomic weight isotopes of lower abundance (e.g., $^{37}$Cl, $^{81}$Br) is not reported.

INDEX TABLE A

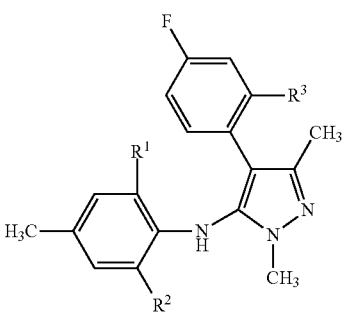

| Compd. No. | R$^1$ | R$^2$ | R$^3$ | m.p. (° C.) |
|---|---|---|---|---|
| 1 (Ex. 3) | F | Br | Cl | 136-137** |
| 2 | Cl | H | Cl | * |
| 3 | Br | H | Cl | * |
| 4 | Cl | H | Br | * |
| 5 | Br | H | Br | * |
| 6 | F | H | Cl | * |
| 7 | F | Br | Br | 143-145 |
| 8 | F | Br | F | 143-144 |
| 9 (Ex. 4) | F | F | F | 156-158** |
| 10 | F | F | Cl | 121-123 |
| 11 | F | Cl | Br | 145-146 |
| 12 | F | Cl | Cl | 137-138 |
| 13 | Cl | Cl | Cl | 188-189 |
| 14 | F | F | Br | 114-116 |
| 15 | Cl | Cl | Br | 191-192 |
| 16 | Cl | Cl | F | 147-149 |

*See Index Table B for for M.S. data.
**See synthesis Example for $^1$H NMR, M.S. and m.p. data.

INDEX TABLE B

| Compd. No. | HPLC M.S. Data |
|---|---|
| 2 | 364 (4.87 min., AP$^+$) |
| 3 | 412 (4.58 min., AP$^+$) |
| 4 | 410 (4.55 min., AP$^+$) |
| 5 | 454 (4.69 min., AP$^+$) |
| 6 | 348 (4.08 min., AP$^+$) |

Biological Examples of the Invention

General protocol for preparing test suspensions for Tests A-H: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-F. Spraying a 40 ppm test suspension to the point of run-off on the test plants was the equivalent of a rate of 160 g/ha. Unless otherwise indicated, the rating values indicate a 40 ppm test suspension was used.

Test A

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 27° C. for 3 days, after which time visual disease ratings were made.

Test B

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 24° C. for 5 days, after which time visual disease ratings were made.

Test C

The test suspension was sprayed to the point of run-off on wheat seedlings. The following day the seedlings were inoculated with a spore suspension of *Septoria nodorum* (the causal agent of *Septoria* glume blotch) and incubated in a saturated atmosphere at 20° C. for 48 h, and then moved to a growth chamber at 20° C. for 9 days, after which time visual disease ratings were made.

Test D

The test suspension was sprayed to the point of run-off on wheat seedlings. The following day the seedlings were inoculated with a spore suspension of *Septoria tritici* (the causal agent of wheat leaf blotch) and incubated in saturated atmosphere at 24° C. for 48 h, and then moved to a growth chamber at 20° C. for 19 days, after which time visual disease ratings were made.

Test E1

Wheat seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 2 days. After 2 days, the test suspension was sprayed to the point of run-off on the wheat seedlings, and then the seedlings were moved back to the growth chamber at 20° C. for 4 days. Upon removal, visual disease ratings were made.

Test E2

The test suspension was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 7 days, after which time visual disease ratings were made.

Test F

The test suspension was sprayed to the point of run-off on wheat seedlings. The following day the seedlings were inoculated with a spore dust of *Blumeria graminis* f. sp. *tritici* (also known as *Erysiphe graminis* f. sp. *tritici*, the causal agent of wheat powdery mildew) and incubated in a growth chamber at 20° C. for 8 days, after which time visual disease ratings were made.

Results for Tests A-F are given in Table A. In the Table, a rating of 100 indicates 100% disease control and a rating of 0 indicates no disease control (relative to the controls). A dash (-) indicates no test results.

TABLE A

| Cmpd. No. | Test A | Test B | Test C | Test D | Test E1 | Test E2 | Test F |
|---|---|---|---|---|---|---|---|
| 1 | 100 | 99 | 90 | 100 | 100 | 100 | 100 |
| 2 | 100 | — | 0 | 100 | — | 95 | 97 |
| 3 | 99 | — | 0 | 100 | — | 99 | 96 |
| 4 | 100 | — | 0 | 100 | — | 97 | 97 |
| 5 | 99 | — | 0 | 100 | — | 97 | 97 |
| 6 | 99 | — | 0 | 100 | — | 0 | 100 |
| 7 | 100 | — | 99 | 100 | — | 100 | 100 |
| 8 | 100 | — | 97 | 100 | — | 100 | 100 |
| 9 | 100 | — | 96 | 100 | — | 96 | 100 |
| 10 | 100 | — | 90 | 100 | — | 100 | 100 |
| 11 | — | — | — | — | — | — | — |
| 12 | — | — | — | — | — | — | — |
| 13 | 100 | — | 0 | 100 | — | 100 | 100 |
| 14 | 100 | — | 86 | 100 | — | 100 | 100 |
| 15 | 100 | — | 0 | 100 | — | 100 | 99 |
| 16 | 100 | — | 97 | 73 | — | 100 | 99 |

What is claimed is:

1. A compound selected from Formula 1, N-oxides and salts thereof, wherein
$R^1$ is F, Cl or Br;
$R^2$ is H, F, Cl or Br; and
$R^3$ is F, Cl or Br.

2. A compound of claim 1 wherein:
$R^1$ is F or Cl; and
$R^2$ is F, Cl or Br.

3. The compound of claim 1 which is selected from the group:
N-(2-bromo-6-fluoro-4-methylphenyl)-4-(2-chloro-4-fluorophenyl)-1,3-dimethyl-1H-pyrazol-5-amine,
4-(2-chloro-4-fluorophenyl)-N-(2-chloro-4-methylphenyl)-1,3-dimethyl-1H-pyrazol-5-amine,
N-(2-bromo-4-methylphenyl)-4-(2-chloro-4-fluorophenyl)-1,3-dimethyl-1H-pyrazol-5-amine,
4-(2-bromo-4-fluorophenyl)-N-(2-chloro-4-methylphenyl)-1,3-dimethyl-1H-pyrazol-5-amine,
4-(2-bromo-4-fluorophenyl)-N-(2-bromo-4-methylphenyl)-1,3-dimethyl-1H-pyrazol-5-amine,
4-(2-chloro-4-fluorophenyl)-N-(2-fluoro-4-methylphenyl)-1,3-dimethyl-1H-pyrazol-5-amine,
N-(2-bromo-6-fluoro-4-methylphenyl)-4-(2-bromo-4-fluorophenyl)-1,3-dimethyl-1H-pyrazol-5-amine,
N-(2-bromo-6-fluoro-4-methylphenyl)-4-(2,4-difluorophenyl)-1,3-dimethyl-1H-pyrazol-5-amine,
N-(2,6-difluoro-4-methylphenyl)-4-(2,4-difluorophenyl)-1,3-dimethyl-1H-pyrazol-5-amine,
4-(2-chloro-4-fluorophenyl)-N-(2,6-difluoro-4-methylphenyl)-1,3-dimethyl-1H-pyrazol-5-amine,
4-(2-bromo-4-fluorophenyl)-N-(2-chloro-6-fluoro-4-methylphenyl)-1,3-dimethyl-1H-pyrazol-5-amine and
N-(2-chloro-6-fluoro-4-methylphenyl)-4-(2-chloro-4-fluorophenyl)-1,3-dimethyl-1H-pyrazol-5-amine.

4. The compound of claim 1 which is selected from the group:
N-(2-bromo-6-fluoro-4-methylphenyl)-4-(2-chloro-4-fluorophenyl)-1,3-dimethyl-1H-pyrazol-5-amine,
4-(2-chloro-4-fluorophenyl)-N-(2-chloro-4-methylphenyl)-1,3-dimethyl-1H-pyrazol-5-amine,
N-(2-bromo-4-methylphenyl)-4-(2-chloro-4-fluorophenyl)-1,3-dimethyl-1H-pyrazol-5-amine,
4-(2-bromo-4-fluorophenyl)-N-(2-chloro-4-methylphenyl)-1,3-dimethyl-1H-pyrazol-5-amine,
4-(2-bromo-4-fluorophenyl)-N-(2-bromo-4-methylphenyl)-1,3-dimethyl-1H-pyrazol-5-amine,
4-(2-chloro-4-fluorophenyl)-N-(2-fluoro-4-methylphenyl)-1,3-dimethyl-1H-pyrazol-5-amine,
N-(2-bromo-6-fluoro-4-methylphenyl)-4-(2-bromo-4-fluorophenyl)-1,3-dimethyl-1H-pyrazol-5-amine,
N-(2-bromo-6-fluoro-4-methylphenyl)-4-(2,4-difluorophenyl)-1,3-dimethyl-1H-pyrazol-5-amine,
N-(2,6-difluoro-4-methylphenyl)-4-(2,4-difluorophenyl)-1,3-dimethyl-1H-pyrazol-5-amine,
4-(2-chloro-4-fluorophenyl)-N-(2,6-difluoro-4-methylphenyl)-1,3-dimethyl-1H-pyrazol-5-amine,
4-(2-bromo-4-fluorophenyl)-N-(2-chloro-6-fluoro-4-methylphenyl)-1,3-dimethyl-1H-pyrazol-5-amine,
N-(2-chloro-6-fluoro-4-methylphenyl)-4-(2-chloro-4-fluorophenyl)-1,3-dimethyl-1H-pyrazol-5-amine,
4-(2-chloro-4-fluorophenyl)-N-(2,6-dichloro-4-methylphenyl)-1,3-dimethyl-1H-pyrazol-5-amine,
4-(2-bromo-4-fluorophenyl)-N-(2,6-difluoro-4-methylphenyl)-1,3-dimethyl-1H-pyrazol-5-amine,
4-(2-bromo-4-fluorophenyl)-N-(2,6-dichloro-4-methylphenyl)-1,3-dimethyl-1H-pyrazol-5-amine and
N-(2,6-dichloro-4-methylphenyl)-4-(2,4-difluorophenyl)-1,3-dimethyl-1H-pyrazol-5-amine.

5. A fungicidal composition comprising (a) a compound of claim 1; and (b) at least one other fungicide.

6. The fungicidal composition of claim 5 wherein component (b) comprises at least one fungicidal compound selected from the group consisting of
(b1) methyl benzimidazole carbamate (MBC) fungicides;
(b2) dicarboximide fungicides;
(b3) demethylation inhibitor (DMI) fungicides;
(b4) phenylamide fungicides;
(b5) amine/morpholine fungicides;
(b6) phospholipid biosynthesis inhibitor fungicides;
(b7) carboxamide fungicides;
(b8) hydroxy(2-amino-)pyrimidine fungicides;
(b9) anilinopyrimidine fungicides;
(b10) N-phenyl carbamate fungicides;
(b11) quinone outside inhibitor (QoI) fungicides;
(b12) phenylpyrrole fungicides;
(b13) quinoline fungicides;
(b14) lipid peroxidation inhibitor fungicides;
(b15) melanin biosynthesis inhibitors-reductase (MBI-R) fungicides;
(b16) melanin biosynthesis inhibitors-dehydratase (MBI-D) fungicides;
(b17) hydroxyanilide fungicides;
(b18) squalene-epoxidase inhibitor fungicides;
(b19) polyoxin fungicides;
(b20) phenylurea fungicides;
(b21) quinone inside inhibitor (QiI) fungicides;
(b22) benzamide fungicides;

(b23) enopyranuronic acid antibiotic fungicides;
(b24) hexopyranosyl antibiotic fungicides;
(b25) glucopyranosyl antibiotic: protein synthesis fungicides;
(b26) glucopyranosyl antibiotic: trehalase and inositol biosynthesis fungicides;
(b27) cyanoacetamideoxime fungicides;
(b28) carbamate fungicides;
(b29) oxidative phosphorylation uncoupling fungicides;
(b30) organo tin fungicides;
(b31) carboxylic acid fungicides;
(b32) heteroaromatic fungicides;
(b33) phosphonate fungicides;
(b34) phthalamic acid fungicides;
(b35) benzotriazine fungicides;
(b36) benzene-sulfonamide fungicides;
(b37) pyridazinone fungicides;
(b38) thiophene-carboxamide fungicides;
(b39) pyrimidinamide fungicides;
(b40) carboxylic acid amide (CAA) fungicides;
(b41) tetracycline antibiotic fungicides;
(b42) thiocarbamate fungicides;
(b43) benzamide fungicides;
(b44) host plant defense induction fungicides;
(b45) multi-site contact activity fungicides;
(b46) fungicides other than fungicides of component (a) and components (b1) through (b45); and
salts of compounds of (b1) through (b46).

7. A fungicidal composition of claim 6; and at least one additional component selected from the group consisting of surfactants, solid diluents and liquid diluents.

8. A method for controlling plant diseases caused by fungal plant pathogens comprising applying to the plant or portion thereof, or to the plant seed, a fungicidally effective amount of a compound of claim 1.

* * * * *